(12) United States Patent
Aramini et al.

(10) Patent No.: US 10,246,448 B2
(45) Date of Patent: Apr. 2, 2019

(54) 4-HYDROXY-2-PHENYL-1,3-THIAZOL-5-YL METHANONE DERIVATIVES AS TRPM8 ANTAGONISTS

(71) Applicant: DOMPÉ FARMACEUTICI S.P.A., Milan (IT)

(72) Inventors: Andrea Aramini, L'Aquila (IT); Gianluca Bianchini, L'Aquila (IT); Samuele Lillini, Chiaravalle (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 0 days.

(21) Appl. No.: 16/061,850

(22) PCT Filed: Dec. 16, 2016

(86) PCT No.: PCT/EP2016/081567
§ 371 (c)(1),
(2) Date: Jun. 13, 2018

(87) PCT Pub. No.: WO2017/108632
PCT Pub. Date: Jun. 29, 2017

(65) Prior Publication Data
US 2018/0319785 A1 Nov. 8, 2018

(30) Foreign Application Priority Data
Dec. 21, 2015 (EP) ...................... 15201788

(51) Int. Cl.
*A61P 11/00* (2006.01)
*A61P 29/00* (2006.01)
*A61P 35/00* (2006.01)
*C07D 417/06* (2006.01)

(52) U.S. Cl.
CPC ............ *C07D 417/06* (2013.01); *A61P 11/00* (2018.01); *A61P 29/00* (2018.01); *A61P 35/00* (2018.01)

(58) Field of Classification Search
CPC ........ C07D 417/06; A61P 11/00; A61P 29/00; A61P 35/00
USPC ....................................................... 514/439
See application file for complete search history.

(56) References Cited

U.S. PATENT DOCUMENTS

| 8,906,946 | B2 * | 12/2014 | Moriconi | ............ | C07D 207/323 |
| | | | | | 514/357 |
| 9,585,875 | B2 * | 3/2017 | Moriconi | ............. | A61K 31/421 |
| 9,856,246 | B2 * | 1/2018 | Moriconi | ............. | A61K 31/421 |
| 2014/0371276 | A1 * | 12/2014 | Moriconi | ............. | A61K 31/421 |
| | | | | | 514/342 |
| 2015/0313854 | A1 | 11/2015 | Belmonte Mart Nez et al. | | |
| 2017/0129881 | A1 * | 5/2017 | Moriconi | ............. | A61K 31/421 |
| 2017/0190678 | A1 * | 7/2017 | Aramini | ............... | C07D 417/04 |

FOREIGN PATENT DOCUMENTS

| WO | WO2006040136 | 4/2006 |
| WO | WO2007017092 | 2/2007 |
| WO | WO2007017093 | 2/2007 |
| WO | WO2007017094 | 2/2007 |
| WO | WO2007080109 | 7/2007 |
| WO | WO2007134107 | 11/2007 |
| WO | WO2009012430 | 1/2009 |
| WO | WO2010103381 | 9/2010 |
| WO | WO2010125831 | 11/2010 |
| WO | WO2013092711 | 6/2013 |
| WO | WO2015197640 | 12/2015 |

OTHER PUBLICATIONS

Moran; British Journal of Pharmacology 2018, 175, 2185-2203. (Year: 2018).*
Andrews; ACS Med. Chem. Lett. 2015, 6, 419-424. (Year: 2015).*
Broad; Expert Opinion on Therapeutic Targets 2009, 13, 69-81. (Year: 2009).*
Belmonte, Carlos, et al., "Wnat causes eye pain?", Curr Ophthalmol Rep (2015) 3, pp. 111-121.
De Groat, William, C., "A neurologic basis for the overactive bladder", Urology 50 (Suppl 6A): 1997, pp. 36-52.
De Petrocellis, Luciano, et al., "Regulation of transient receptor potential channels of melastatin type 8 (TRPM8): Effect of cAMP, cannabinoid CB1 receptors and endovanilloids", Experimental Cell Research 313 (2007) pp. 1911-1920.
EESR for EP15201788.5 dated Feb. 10, 2016.
Everaerts, Wouter, et al., "On the origin of bladder sensing: Tr(i)ps in urology", Neurourology and Urodynamics 27 (2008), pp. 264-273.
International Search Report for PCT/EP2016/081567 dated Feb. 3, 2017.

(Continued)

*Primary Examiner* — Daniel R Carcanague
(74) *Attorney, Agent, or Firm* — Hueschen and Sage

(57) ABSTRACT

The invention relates to compounds acting as antagonists of Transient Receptor Potential cation channel subfamily M member 8 (TRPM8), and having formula (I):

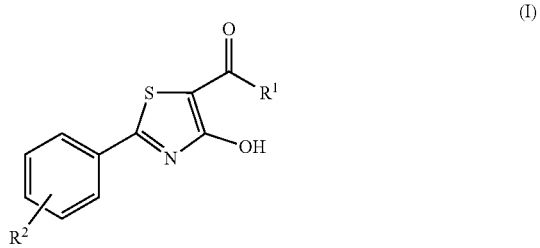

Said compounds are useful in the treatment of diseases associated with activity of TRPM8 such as pain, ischaemia, neurodegeneration, stroke, psychiatric disorders, itch, irritable bowel diseases, cold-induced and/or exacerbated-respiratory disorders, urological disorders, corneal disorders associated to disturbances in the production of the tears and/or altered blinking such as epiphora and dry eye disease.

14 Claims, No Drawings

(56) References Cited

OTHER PUBLICATIONS

Kerdesky, Francis, A.J., et al., "4-Hydroxythiazole inhibitors of 5-lipoxygenase", J. Med. Chem., 1991, 34, pp. 2158-2165.

Lazzeri, Massimo, et al., "TRP family proteins in the lower urinary tract: translating basic science into new clinical prospective", Ther Adv Urol (2009) 1(1), pp. 33-42.

McKemy, David, D., et al., "Identification of a cold receptor reveals a general role for TRP channels in thermosensation", Nature vol. 416, Mar. 7, 2002, pp. 52-58.

Mukerji, Gaurav, et al., "Pain during ice water test distinguishes clinical bladder hypersensitivity from overactivity disorders", BMC Urology, 2006, 6:31.

Nilius, Bernd, "TRP channels in disease", Biochimica et Biophysica Acta 1772 (2007), pp. 805-812.

Nilius, Bernd, et al., "Gating of TRP channels: a voltage connection?", J. Physiol 567.1 (2005), pp. 35-44.

Nilius, Bernd, et al., "Transient receptor potential cation channels in disease", Physiol Rev 87 (2007) pp. 165-217.

Nilius, Bernd, et al., "TRP channels in disease", Sci. STKE 2005 (295), re8, pp. 1-9.

Peier, Andrea, M. et al., "A TRP channel that senses cold stimuli and menthol", Cell, vol. 108, Mar. 8, 2002, pp. 705-715.

Proudfoot, Clare, J., et al., "Analgesia mediated by the TRPM8 cold receptor in chronic neuropathic pain", Current Biology, 16, Aug. 22, 2006, pp. 1591-1605.

Quallo, Talisa, et al., "TRPM8 is a neuronal osmosensor that regulates eye blinking in mice", Nature Communications, 6:7150, 2015, pp. 1-12.

Rohács, Tibor, et al., PI(4,5)P2 regulates the activation and desensitization of TRPM8 channels through the TRP domain, Nature Neuroscience, vol. 8, No. 5, May 2005, pp. 626-634.

Tsuge, O., et al., "Studies of acyl and thioacyl isocyanates—XIII: The reactions of benzoyl and thibenzoyl isocyanates with sulfonium ylides and with diazoalkanes", Tetrahedron, vol. 29 (1973) pp. 1983-1990.

Vanden-Abeele, Fabien, et al., "Membrane transport, structure function, and biogenesis: Ca2+-independent phospholipase A2-dependent gating of TRPM8 by lysophospholipids", J. Biol. Chem, 281 (2006) pp. 40174-40182.

Voets, Thomas, et al., "Sensing with TRP channels", Nature Chemical Biology vol. 1, No. 2, Jul. 2005, pp. 85-92.

Wissenbach, Ulrich, et al., "TRP channels as potential drug targets", Biology of the Cell, 96 (2004) pp. 47-54.

Xing, Hong, et al., "TRPM8 mechanism of autonomic nerve response to cold in respiratory airway", Molecular Pain 4:22 (2008).

* cited by examiner

US 10,246,448 B2

4-HYDROXY-2-PHENYL-1,3-THIAZOL-5-YL METHANONE DERIVATIVES AS TRPM8 ANTAGONISTS

BRIEF DESCRIPTION OF THE INVENTION

The present invention relates to 2-phenyl-4-hydroxy-1,3-thiazol-5-yl methanone derivatives that are useful for the prevention, reduction of the risk of, amelioration and/or treatment of diseases associated with the activity of the Transient Receptor Potential cation channel subfamily M member 8 (hereinafter TRPM8) also known as Cold Menthol Receptor 1 (CMR-1), and in particular for the prevention, reduction of the risk of, amelioration and/or treatment of itch, irritable bowel diseases, cold induced and/or exacerbated respiratory disorders, ischaemia, pain, neurodegeneration, psychiatric disorders, stroke, urological disorders, corneal disorders associated to disturbances in the production of the tears and/or altered blinking such as epiphora and dry eye disease. The invention further relates to pharmaceutical compositions containing the above compounds.

BACKGROUND OF THE INVENTION

Transient Receptor Potential (TRP) channels are one of the largest group of ion channels and, based on their sequence homology, are classified into 6 sub-families (TRPV, TRPM; TRPA, TRPC, TRPP and TRPML). TRP channels are cation-selective channels activated by several physical (such as temperature, osmolarity and mechanical stimuli) and chemical stimuli. TRPM8, which was cloned in 2002, is a non-selective cation channel of the TRP family expressed on a subpoputation of somatic sensory nerves on dorsal root ganglion and trigeminal ganglia that causes sensory nerve excitation. It is activated by mild cold temperatures and synthetic cool-mimetic compounds such as menthol, eucalyptol and icilin [McKemy D. D. et al. *Nature* (2002) 416, 52-58; Railer A. M. et al, *Cell* (2002) 108, 705-715]. Like several other TRP channels, TRPM8 is also gated by voltage [Nilius B. et al., *J. Physiol.* (2005) 567, 35-44]. The voltage dependence of TRPM8 is characterized by a strong outward rectification at depolarized transmembrane potential and a rapid and potential-dependent closure at negative membrane potentials. Cooling agents and menthol application shifts the activation curve towards more negative potentials, increasing the possibility for the opening of the channel and boosting inward currents at physiological membrane potentials. Other endogenous factors, such as phospholipase $A_2$ products [Vanden Abeele F. et al., J. Biol. Chem. (2006) 281, 40174-40182], endocannabinoids [De Petrocellis L. et al., Exp. Cell. Res. (2007) 313, 1911-1920] and PIP2 [Rohacs T. et al., Nat. Neurosci. (2005) 8, 626-634] also participate in channel regulation.

There is a lot of direct and indirect evidence of a pivotal role of TRPM8 channel activity in diseases such as itch, irritable bowel diseases, cold induced and/or exacerbated respiratory disorders, ischaemia, pain, neurodegeneration, psychiatric disorders, stroke, urological disorders, dry eye syndrome and epiphora.

For example, it has been demonstrated that TRP channels transduce reflex signals that are involved in the overactive bladder of patients with damaged or abnormal spinal reflex pathways [De Groat W. C. et al., Urology (1997) 50, 36-52]. TRPM8 is activated by temperatures between 8° C. and 28° C. and expressed on the primary nociceptive neurons, including bladder urothelium, dorsal root ganglia, A-delta and C-fibers. The intravesical ice water or menthol also induce C-fiber mediated spinal micturition reflex in patients with urgency and urinary incontinence [Everaerts W. et al., Neurol. Urodyn. (2008) 27, 264-73].

Furthermore, TRPM8 is known to regulate $Ca^{2+}$ concentration influxes in response to cold temperature or pharmacological stimuli. Finally, the potential role of TRPM8 in cold-induced asthma and in asthma exacerbation has been proposed, suggesting TRPM8 also a relevant target for the management of these pathologies [Xing H. et al., *Molecular Pain* (2008), 4, 22-30].

The expression of the channel in brain, lung, bladder, gastrointestinal tract, blood vessels, prostate and immune cells provide further possibility for therapeutic modulation of the activity of TRPM8 in a wide range of pathologies. In particular, the disorders or diseases that have been proven to be affected by the modulation of TRPM8 are pain such as chronic pain, neuropathic pain including cold allodynia and diabetic neuropathy, postoperative pain, osteoarthritic pain, rheumatoid arthritic pain, cancer pain, neuralgia, neuropathies, algesia, fibromyalgia, nerve injury, migraine, headaches; ischaemia, neurodegeneration, stroke, psychiatric disorders, including anxiety and depression, and itch, irritable bowel diseases, cold induced and/or exhacerbated respiratory disorders such as cold induced and/or exhacerbated pulmonary hypertension, asthma and COPD; urological disorders such as painful bladder syndrome, interstitial cystitis, detrusor overactivity (overactive bladder), urinary incontinence, neurogenic detrusor overactivity (detrusor hyperflexia), idiopathic detrusor overactivity (detrusor instability), benign prostatic hyperplasia, lower urinary tract disorders and lower urinary tract symptoms [Nilius B. et al. *Science STKE* (2005), 295, re8; Voets T. et al., *Nat. Chem. Biol.* (2005), 1, 85-92; Mukerji G. et al., *Urology* (2006), 6, 31-36; Lazzeri M. et al., *Ther. Adv. Urol.* (2009), 1, 33-42; Nilius B. et al., *Biochim. Biophys. Acta* (2007), 1772, 805-12; Wissenbach U. et al., *Biol. Cell.* (2004), 96, 47-54; Nilius B. et al., *Physiol. Rev.* (2007), 87, 165-217; Proudfoot C. J. et al., *Curr. Biol.* (2006), 16, 1591-1605].

Furthermore, it has been demonstrated that TRPM8 inhibition is effective in the treatment of corneal disorders associated to disturbances in the production of the tears and/or altered blinking such as epiphora (US2015313854) and dry eye disease (Quallo et al, *Nature Communications* (2015) 6: 7150, DOI: 10.1038/ncomms8150, Belmonte et al, *Curr Ophtalmol Rep* (2015), 3:111-121)

Along the last few years, several classes of non peptide TRPM8 antagonists have been disclosed. WO 2006/040136, WO 2007/017092, WO 2007/017093, WO 2007/017094, and WO 2007/080109 describe benzyloxy derivatives as TRPM8 antagonists for the treatment of urological disorders; WO 2007/134107 describes phosphorous-bearing compounds as TRPM8 antagonists for the treatment of TRPM8-related disorders; WO 2009/012430 describes sulfonamides for the treatment of diseases associated with TRPM8; WO 2010/103381 describes the use of spirocyclic piperidine derivatives as TRPM8 modulators in prevention or treatment of TRPM8-related disorders or diseases; WO 2010/125831 describes sulfamoyl benzoic acid derivatives as modulators of the TRPM8 receptor and their use in the treatment of inflammatory, pain and urological disorders; and WO 2013/092711 describes 2-aryl oxazole and thiazole derivatives as TRPM8 receptor modulators and their use in prevention, reduction of the risk of, amelioration and/or treatment of urological-related disorders.

A therapeutic area in which there is still a particularly high need for the development of antagonists of TRPM8 is that of urological disorders and associated pain. In fact, traditional drugs and medications currently available for the treatment of urinary incontinence and disorders are characterized by several side effects. For example, at the moment, the therapy of overactive bladder syndrome is based on the use of drugs, especially anticholinergic agents that affect peripheral neural control mechanisms or bladder detrusor smooth muscle contraction. These drugs inhibit parasympathetic nerves exerting a direct spasmolytic effect on the muscle of the bladder. The result of this action is the decrease of intravesicular pressure, an increase in capacity and a reduction in the frequency of bladder contraction. However, the use of anticholinergic agents is associated with serious side effects, such as dry mouth, abnormal visions, constipation and CNS disturbances, that impair the overall patient compliance. The inadequacies of the actual therapies highlight the need for novel, efficacious and safe drugs with fewer side effects.

SUMMARY OF THE INVENTION

The aim of the present invention is to provide novel antagonists of TRPM8.

The present inventors have now found a class of 2-phenyl-4-hydroxy-1,3-thiazol-5-yl methanone compounds acting as selective antagonists of Transient Receptor Potential cation channel subfamily M member 8 (hereinafter referred to as TRPM8), suited with good oral bioavailability and satisfying the above desiderata.

These compounds are useful in the treatment of a disease associated with the activity of TRPM8, preferably a disease deriving from overexpression and/or hyperactivity of TRPM8 receptor.

DETAILED DESCRIPTION OF THE INVENTION

A first object of the present invention are compounds of formula (I):

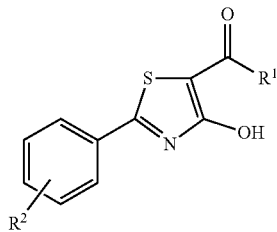

wherein
$R^1$ is an unsubstituted or substituted 5, 6 or 7-membered, aliphatic or aromatic heterocycle group containing 1, 2, 3 or 4 heteroatoms selected from N, O and S;
$R^2$ is selected from hydrogen, $C_1$-$C_2$ alkyl, F, Cl and OH;
and pharmaceutically acceptable salts thereof.

The term "substituted" herein refers to mono- or polysubstitution by a named (or undefined) substituent to the extent that such a single or multiple substitution is chemically allowed.

Preferably, said 5, 6 or 7-membered, aliphatic or aromatic heterocycle is unsubstituted or substituted with one or more groups independently selected from $C_1$-$C_3$ alkyl or cycloalkyl, Cl and F. Preferably, said $C_1$-$C_3$ alkyl is methyl.

According to a preferred embodiment the heterocycle is substituted with $R^3$ and $R^4$ that taken together can form a saturated cyclic moiety, preferably cyclobutane, cyclopentane or cyclohexane.

According to a preferred embodiment the heterocycle is unsubstituted.

Preferably, $R^1$ is selected from the group consisting, of oxazolidinyl, oxolanyl, pyrrolidinyl, oxazinanyl, morpholinyl, piperidinyl, methylpyrrolidinyl, pyrrolyl, methyloyrrolyl, furanyl, thiophenyl, pyridinyl, imidazolyl, pyrazolyl, oxadiazolyl and oxazolyl.

More preferably, $R^1$ is selected from the group consisting of 1,2-oxazolidin-2-yl, 1,3-oxazolidin-3-yl, oxolan-2-yl, pyrrolidin-1-yl, 1,2-oxazinan-2-yl, 1,3-oxazinan-3-yl, morpholin-4-yl, piperidin-1-yl, pyrrolidin-2-yl, 1-methylpyrrolidin-2-yl, 1H-pyrrol-2-yl, 1-methyl-1H-pyrrol-2-yl, furan-2-yl, thiophen-2-yl, 1H-pyrrol-1-yl, pyridin-2-yl, pyridin-3-yl, pyridin-4-yl, 1H-imidazol-1-yl and 1H-pyrazol-1-yl.

Preferably, $R^2$ is F or OH.
More preferably, $R^2$ is 3-F or 2-OH
In an embodiment according to the invention,
$R^1$ is oxazolidinyl and $R^2$ is F or OH.
In another embodiment according to the invention,
$R^1$ is oxolanyl and $R^2$ is F or OH.
In another embodiment according to the invention,
$R^1$ is pyrrolidinyl and $R^2$ is F or OH.
In another embodiment according to the invention,
$R^1$ is oxazinanyl and $R^2$ is F or OH.
In another embodiment according to the invention,
$R^1$ is morpholinyl and $R^2$ is F or OH.
In another embodiment according to the invention,
$R^1$ is piperidinyl and $R^2$ is F or OH.
In another embodiment according to the invention,
$R^1$ is methylpyrrolidinyl and $R^2$ is F or OH.
In another embodiment according to the invention,
$R^1$ is pyrrolyl and $R^2$ is F or OH.
In another embodiment according to the invention,
$R^1$ is methylpyrrolyl and $R^2$ is F or OH.
In another embodiment according to the invention,
$R^1$ is furanyl and $R^2$ is F or OH.
In another embodiment according to the invention,
$R^1$ is thiophenyl and $R^2$ is F or OH.
In another embodiment according to the invention,
$R^1$ is pyridinyl and $R^2$ is F or OH.
In another embodiment according to the invention,
$R^1$ is imidazolyl and $R^2$ is F or OH.
In another embodiment according to the invention,
$R^1$ is pyrazolyl and $R^2$ is F or OH.

Preferred compounds of formula (I) according to the invention are selected from:
[2-(3-fluorophenyl)-4-hydroxy-1,3-thiazol-5-yl](1,2-oxazolidin-2-yl)methanone (1)
[4-hydroxy-2-(2-hydroxyphenyl)-1,3-thiazol-5-yl](1,2-oxazolidin-2-yl)methanone (2)
[2-(3-fluorophenyl)-4-hydroxy-1,3-thiazol-5-yl](1,3-oxazolidin-3-yl)methanone (3)
[4-hydroxy-2-(2-hydroxyphenyl)-1,3-thiazol-5-yl](1,3-oxazolidin-3-yl)methanone (4)
[2-(3-fluorophenyl)-4-hydroxy-1,3-thiazol-5-yl](oxolan-2-yl)methanone (5)
[4-hydroxy-2-(2-hydroxyphenyl)-1,3-thiazol-5-yl](oxolan-2-yl)methanone (6)
[2-(3-fluorophenyl)-4-hydroxy-1,3-thiazol-5-yl](pyrrolidin-1-yl)methanone (7)
[4-hydroxy-2-(2-hydroxyphenyl)-1,3-thiazol-5-yl](1,2-oxazinan-2-yl)methanone (8)
[2-(3-fluorophenyl)-4-hydroxy-1,3-thiazol-5-yl](1,2-oxazinan-2-yl)methanone (9)
[2-(3-fluorophenyl)-4-hydroxy-1,3-thiazol-5-yl](1,3-oxazinan-3-yl)methanone (10)

[4-hydroxy-2-(2-hydroxyphenyl)-1,3-thiazol-5-yl](1,3-oxazinan-3-yl)methanone (11)
[2-(3-fluorophenyl)-4-hydroxy-1,3-thiazol-5-yl](morpholin-4-yl)methanone (12)
[4-hydroxy-2-(2-hydroxyphenyl)-1,3-thiazol-5-yl](morpholin-4-yl)methanone (13)
[2-(3-fluorophenyl)-4-hydroxy-1,3-thiazol-5-yl](piperidin-1-yl)methanone (14)
[2-(3-fluorophenyl)-4-hydroxy-1,3-thiazol-5-yl](pyrrolidin-2-yl)methanone (15)
[2-(3-fluorophenyl)-4-hydroxy-1,3-thiazol-5-yl](1-methyl-pyrrolidin-2-yl)methanone (16)
[2-(3-fluorophenyl)-4-hydroxy-1,3-thiazol-5-yl](1H-pyrrol-2-yl)methanone (17)
[2-(3-fluorophenyl)-4-hydroxy-1,3-thiazol-5-yl](1-methyl-1H-pyrrol-2-yl)methanone (18)
[2-(3-fluorophenyl)-4-hydroxy-1,3-thiazol-5-yl](furan-2-yl)methanone (19)
[2-(3-fluorophenyl)-4-hydroxy-1,3-thiazol-5-yl](thiophen-2-yl)methanone (20)
[2-(3-fluorophenyl)-4-hydroxy-1,3-thiazol-5-yl](1H-pyrrol-1-yl)methanone (21)
[2-(3-fluorophenyl)-4-hydroxy-1,3-thiazol-5-yl](pyridin-2-yl)methanone (22)
[2-(3-fluorophenyl)-4-hydroxy-1,3-thiazol-5-yl](pyridin-3-yl)methanone (23)
[2-(3-fluorophenyl)-4-hydroxy-1,3-thiazol-5-yl](pyridin-4-yl)methanone (24)
[2-(3-fluorophenyl)-4-hydroxy-1,3-thiazol-5-yl](1H-imidazol-1-yl)methanone (25)
[2-(3-fluorophenyl)-4-hydroxy-1,3-thiazol-5-yl](1H-pyrazol-1-yl)methanone (26)
[2-(3-fluorophenyl)-4-hydroxy-1,3-thiazol-5-yl](1,2-oxazepan-2-yl)methanone (27)
[2-(3-fluorophenyl)-4-hydroxy-1,3-thiazol-5-yl](5-oxa-6-azaspiro[2.4]heptan-6-yl)methanone (28)
[2-(3-fluorophenyl)-4-hydroxy-1,3-thiazol-5-yl](5-methyl-1,2-oxazolidin-2-yl)methanone (29)
[2-(3-fluorophenyl)-4-hydroxy-1,3-thiazol-5-yl](hexahydro-2H-cyclopenta[d][1,2]oxazol-2-yl)methanone (30)
[2-(3-fluorophenyl)-4-hydroxy-1,3-thiazol-5-yl](1H-1,2,3-triazol-1-yl)methanone (31) and
[2-(3-fluorophenyl)-4-hydroxy-1,3-thiazol-5-yl](1-methyl-1H-tetrazol-5-yl)methanone (32), The most preferred compounds of formula (I) according to the invention are selected from:
[2-(3-fluorophenyl)-4-hydroxy-1,3-thiazol-5-yl](1,2-oxazolidin-2-yl)methanone (1)
[4-hydroxy-2-(2-hydroxyphenyl)-1,3-thiazol-5-yl](1,2-oxazolidin-2-yl)methanone (2)
[4-hydroxy-2-(2-hydroxyphenyl)-1,3-thiazol-5-yl](1,2-oxazinan-2-yl)methanone (8) and
[2-(3-fluorophenyl)-4-hydroxy-1,3-thiazol-5-yl](1,2-oxazinan-2-yl)methanone (9).

As will be shown in the experimental section, the above four compounds are characterized by a very high potency and a high intristic clearance half life.

As it will be described in details in Example 33, the present inventors have found that the above compounds 1-32 are potent antagonists of TRPM8. The TRPMB antagonistic activity of all the compounds was determined in vitro by measuring changes in intracellular calcium levels using a $Ca^{2+}$ sensitive fluorescent dye both after injection of Icilin and after injection of Coolin Agent 10; all of the above compounds have shown an antagonistic activity with a $IC_{50}$ below 2 µM in both tests, as shown in Table 1.

Moreover as it will be described in details in Example 34, all the above compounds were tested in the vitro cold stimulation assay, showing a $IC_{50}$ below 2 µM, as shown in Table 1.

Thus, a second object of the present invention are the above compounds of formula (I) for use as antagonists of TRPM8, preferably of human TRFM8.

Finally, as it will be described in details in Example 35, all compounds of the invention were tested for metabolic stability in rat microsomes, with compounds (1), (2), (8) and (9) showing the highest intrinsic clearance half-life.

Accordingly, a third object of the present invention are the above compounds for use as medicaments. A fourth object of the present invention are the above compounds for use in the prevention, reduction of the risk of, amelioration and/or treatment of a disease associated with activity of TRPM8, preferably a disease deriving from overexpression and/or hyperactivity of TRPM8 receptor.

According to the present invention, by "overexpression and/or hyperactivity of TRPM8 receptor" it is meant an expression and/or activity of TRPM8 receptor higher than physiological level.

According to the present invention, by "disease that is associated with activity of TRPM8" it is preferably meant a disease selected from pain, itch, irritable bowel diseases, cold induced and/or exhacerbated respiratory disorders, ischaemia, neurodegeneration, stroke, urological disorders, psychiatric disorders and corneal disorders associated to disturbances in the production of the tears and/or altered blinking.

According to a preferred embodiment, said pain is selected from chronic pain, cancer pain, neuropathic pain, including cold allodynia, postoperative pain, neuralgia, neuropathies, including diabetic neuropathy, fibromyalgia, algesia, pain associated to nerve injury, migraine, headache. According to a further preferred embodiment said pain is pain of inflammatory origin, preferably associated to osteoarthritis and rheumatoid arthritis.

Preferably, said cold-induced and/or exhacerbated respiratory disorder is selected from cold-induced and/or exhacerbated-pulmonary hypertension, COPD and asthma.

Preferably, said urological disorders are selected from painful bladder syndrome, interstitial cystitis, detrusor overactivity (also known as overactive bladder), urinary incontinence, neurogenic detrusor overactivity (also known as detrusor hyperflexia), idiopathic detrusor overactivity (also known as detrusor instability), benign prostatic hyperplasia, lower urinary tract disorders and lower urinary tract symptoms.

Preferably, said psychiatric disorders are selected from anxiety and depression.

Preferably, said corneal disorders associated to disturbances in the production of the tears and/or altered blinking are selected from epiphora and dry eye disease.

A fifth object of the present invention are pharmaceutical compositions comprising the at least one of the above said compounds of formula (I) in combination with pharmaceutically acceptable excipients and/or diluents.

According to a preferred embodiment said pharmaceutical composition is for the prevention, reduction of the risk of, amelioration and/or treatment of a disease associated with activity of TRPM8, preferably a disease deriving from overexpression and/or hyperactivity of TRPM8 receptor.

According to an embodiment, said pharmaceutical composition contains at least one of the above compounds of formula (I) as the sole active principle(s). According to an alternative embodiment, said pharmaceutical composition contains at least one of the above compounds of formula (I) in association with at least one other active principle.

According to a preferred embodiment of the invention, also in combination with the preceding embodiments, the pharmaceutical compositions may be for intravesical, intravenous, topical or oral administration.

The compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

A sixth object of the present invention is a therapeutic method for the prevention, reduction of the risk of, amelioration and/or treatment of said disease associated with activity of TRPM8, preferably a disease deriving from overexpression and/or hyperactivity of TRPM8 receptor, comprising administering the above compound of formula (I) in a subject in need thereof.

The compounds of the invention can be administered as the sole active principles or in combination with other therapeutically active compounds.

The administration of the compounds of the invention can be effected by intravesical instillation, by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day optionally divided in multiple administrations.

The present invention shall be illustrated by means of the following examples which re not construed to be viewed as limiting the scope of the invention.

EXAMPLES

Synthesis of Preferred Compounds

The compounds listed in Table 1 have been synthetised following the procedures described in the following examples.
Materials and Methods
Materials and Methods All reagents were purchased from Sigma-Aldrich, Fluorochem and Alfa Aesar and used without further purification. Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, bs=broad signal. Coupling constants (J values) are given in hertz (Hz). Analytical HPLC-MS spectra were recorded on a Thermo Finnigan Surveyor coupled with a Thermo Finnigan LCC) DECA XP-PLUS apparatus and equipped with a C18 (10 μM, 4.6 mm×150 mm) Phenomenex Gemini reverse phase column. The eluent mixture consisted of 10 mM (pH 4.2) ammonium formate/tonic acid buffer and acetonitrile used according the gradient from 90:10 to 10:90 at a flow rate of 0.200 mL min. All MS experiments were performed using electrospray ionization (ESI) in positive and negative ion mode. All reactions were monitored by thin layer chromatography (TLC) carried out on Grace Resolv Davisil silica gel plates 250 μm thick, 60 F254, visualized by using UV (254 nm) or stains such as $KMnO_4$, p-anisaldehyde, and ceric ammonium molybdate (CAM). Chromatographic purifications were carried out on silica gel columns with Grace Resolv Davisil silica 60. All organic solutions were dried over anhydrous $Na_2SO_4$ or $MgSO_4$ and concentrated on a rotary evaporator. All compounds used for biological assays are at least of 98% purity based on HPLC analytical results monitored with 220 and 254 nm wavelengths, unless otherwise noted.

General Procedure
Synthesis of Intermediates

Synthesis of 3-fluorobenzenecarbothioamide (Intermediate a)

A 100 mL round-bottomed flask equipped with condenser and magnetic stirrer was charged with 3-fluorobenzoamide (2.0 g, 14.4 mmol), which was dissolved in 30 mL of THF, then Lawesson's reagent was added to the solution (3.5 g, 8.64 mmol). The mixture was heated to 60° C. and stirred overnight; the transformation was monitored by TLC (Eluent: n-hexane/EtOAc 7:3). The solution was cooled at room temperature and the solvent removed by vacuum distillation.

The crude was purified by flash chromatography (Eluent: n-hexane/EtOAc 7:3) from which 3-fluorobenzenecarbothioamide was obtained as a yellow solid (2.0 g, 12.9 mmol, Y=89%).

$^1$H-NMR (CDCl$_3$): δ 7.80-7.55 (bs, 1H, N$\underline{H}_2$), 7.66-7.60 (m, 2H), 7.44-7.37 (m, 1H), 7.27-720 (m, 1H), 7.30-7.00 (bs, 1H, N$\underline{H}_2$).
MS (ES$^{1+}$) m/z: 156.11 [M+H]$^+$.

Synthesis of ethyl 2-(3-fluorophenyl)-4-hydroxy-1,3-thiazole-5-carboxylate (Intermediate b)

A microwave vial equipped with a magnetic stirrer was charged with 3-fluorobenzenecarbothioamide (0.5 g, 3.22 mmol) dissolved in dry ethanol (8 mL), diethylbromomalonate was added (0.055 mL, 3.22 mmol) and the vial tightly stoppered. The solution was irradiated in a microwave apparatus at 100° C. for 30 minutes. Ethyl 2-(3-fluorophenyl)-4-hydroxy-1,3-thiazole-5-carboxylate was obtained as a yellow solid after crystallization from ethanol (0.439 g, 1.64 mmol, Y=51%).

$^1$H-NMR (CDCl$_3$): δ 9.94 (bs, 1H, O$\underline{H}$), 7.80-7.70 (m, 2H), 7.49-7.41 (m, 1H), 7.2-7.17 (m, 1H), 4.43 (q, 2H, J=7.1 Hz), 1.42 (t, 3H, J=7.1 Hz).
MS (ES$^{1+}$) m/z: 267.81 [M+H]$^+$.

Synthesis of ethyl 2-(3-fluorophenyl)-4-methoxy-1,3-thiazole-5-carboxylate (Intermediate c)

A 25 mL round-bottomed flask equipped with a magnetic stirrer was charged with Ethyl 2-(3-fluorophenyl)-4-hydroxy-1,3-thiazole-5-carboxylate (0.100 g, 0.374 mmol) which was dissolved in dry THF (3 mL) and DMF (2.5 mL), the solution was treated with NaH (60-65% oil dispersion, 0.022 g, 1.5 eq) and methyl iodide (0.140 mL, 7 eq.) and stirred overnight at room temperature. The reaction was quenched in water and extracted in ethyl acetate (20 mL, 3 times), the organics were collected and washed with saturated sodium bicarbonate and brine then anhydrified over dry sodium sulphate. The crude was purified over silica gel (Eluent: n-hexane/ethyl acetate 9:1). Ethyl 2-(3-fluorophenyl)-4-methoxy-1,3-thiazole-5-carboxylate was obtained as a yellow solid (0.053 g, 0.19 mmol, Y=50%).

$^1$H-NMR (CDCl$_3$): δ 7.69-7.25 (m, 2H), 7.47-7.41 (m, 1H), 7.23-7.16 (m, 1H), 4.36 (q, 2H, J=7.2 Hz), 4.25 (s, 3H), 1.39 (t, 3H, J=7.2 Hz).
MS (ES$^{1+}$) m/z: 282.08 [M+H]$^+$.

Synthesis of 2-(3-fluorophenyl)-4-methoxy-1,3-thiazole-5-carboxylic acid (Intermediate d)

A 25 mL round-bottomed flask equipped with a magnetic stirrer was charged with Ethyl 2-(3-fluorophenyl)-4-methoxy-1,3-thiazole-5-carboxylate (0.097 g, 0.344 mmol) which was dissolved in ethanol (3 mL) and water (0.020 mL). Then KOH was added (0.193 g, 3.44 mmol) and the solution was stirred overnight at room temperature. The mixture was diluted in water (15 mL), acidified with HCl 2N to pH 2 and extracted in ethyl acetate (20 mL×2). The organic layers were collected and washed with water and brine, then anhydrified over dry sodium sulphate. 2-(3-fluorophenyl)-4-methoxy-1,3-thiazole-5-carboxylic add was obtained as a yellow solid (0.077 g, 0.304 mmol, Y=88%).
$^1$H-NMR (CDCl$_3$): δ 7.76-7.71 (m, 2H), 7.50-7.43 (m, 1H), 7.26-7.19 (m, 1H), 4.32 (s, 3H).
MS (ES$^{1-}$) m/z: 252.21 [M−H]$^−$.

Synthesis of 2-(3-fluorophenyl)-4-methoxy-1,3-thiazole-5-carbonyl chloride (Intermediate e)

A 25 mL round-bottomed flask equipped with a magnetic stirrer and a water cooled condenser was charged with 2-(3-fluorophenyl)-4-methoxy-1,3-thiazole-5-carboxylic acid (0.049 g, 0.193 mmol) and 5 mL of dry DCM at room temperature. At the same temperature the solution was treated with an excess of thionyl chloride (0.028 mL, 0.387 mmol) and a catalytic amount of DMF (0.002 mL) then refluxed for 2.5 hours. The solution was cooled then volatiles were removed under reduced pressure. The oily residue was stripped a few times with toluene to further remove residual thionyl chloride. 2-(3-fluorophenyl)-4-methoxy-1,3-thiazole-5-carbonyl chloride as pale yellow al was obtained (0.052 g, 0.0193 mmol, Y=95%) and used without further purification.

Synthesis of 2-(3-fluorophenyl)-N,4-dimethoxy-N-methyl-1,3-thiazole-5-carboxamide (Intermediate f)

In a 25 mL round-bottomed flask equipped with a magnetic stirrer, 2-(3-fluorophenyl)-4-methoxy-1,3-thiazole-5-carbonyl chloride (0.052 g, 0.193 mmol) was dissolved in dry DCM (5 mL) and cooled to 0° C. with an ice bath. This solution was treated with a mixture of N,O-dimethylhydroxylamine hydrochloride (0.038 g, 0.386 mmol), triethylamine (0.1 mL) and DCM (2 mL), and stirred at the same temperature for 45 minutes. As checked by LC-MS, the reaction was complete thus it was quenched and worked up as it follows: the mixture was dilute with DOM (50 mL) and washed with water (10 mL×2) and brine (10 mL) dried over anhydrous sodium sulphate and the solvent vacuum distilled. 2-(3-fluorophenyl)-N, 4-dimethoxy-N-methyl-1,3-thiazole-5-carboxamide (0.060 g, 0.20 mmol, Y=95%) was obtained as an oily solid and used in the next synthetic step.
$^1$H-NMR (CDCl$_3$): δ 7.79-7.71 (m, 2H), 7.48-7.40 (m, 1H), 7.22-7.14 (m, 1H), 4.25 (s, 3H), 3.77 (s, 3H), 3.35 (s, 3H).
MS (ES$^{1+}$) m/z: 297.32 [M+H]$^+$.

Synthesis of 4-methoxy-2-(2-methoxyphenyl)-1,3-thiazole-5-carbonyl chloride (Intermediate g)

Starting from 2-methoxybenzene-1-carbothioamide (0.152 g, 1.0 mmol), 4-methoxy-2-(2-methoxyphenyl)-1,3-thiazole-5-carbonyl chloride was prepared as described in the synthesis of Intermediate e with a yield of 27% over 4 steps.

Synthesis of 2-aryl-4-methoxy-1,3-thiazole (Intermediate h)

A microwave vial equipped with a magnetic stirrer was charged with 3-fluorobenzenecarbothioamide or 2-methoxybenzene-1-carbothioamide (1 mmol) dissolved in dry ethanol (3 mL), methyl bromoacetate (1 mmol) was added and the vial tightly stoppered. The solution was irradiated in a microwave apparatus at 100° C. for 15 minutes. 2-(3-fluorophenyl)-4-methoxy-1,3-thiazole (or 4-methoxy-2-(2-methoxyphenyl)-1,3-thiazole) was obtained as a yellow oil after flash chromatographic purification (n-hexane:ethyl acetate 9:1).
General Procedure for Friedel-Crafts Acylation of Aromatics:

To a solution of aromatic reagent (4 mmol) and 2-(3-fluorophenyl)-4-methoxy-1,3-thiazole-5-carbonyl chloride (6 mmol) in nitromethane (5 ml), Zn(OTf)$_2$.6H$_2$O (0.4 mmol) was added successfully. The mixture was stirred at room temperature overnight. The reaction mixture was then treated with saturated aqueous NaHCO$_3$ (10 ml) and extracted with chloroform (20 ml×2). The combined organic solution was dried over anhydrous Na$_2$SO$_4$, filtered and concentrated in vacuum. The corresponding product was obtained after flash chromatography purification.

Example 1

Synthesis of [2-(3-fluorophenyl)-4-hydroxy-1,3-thiazol-5-yl](1,2-oxazolidin-2-yl)methanone (1)

Starting from 2-(3-fluorophenyl)-4-methoxy-1,3-thiazole-5-carbonyl chloride (intermediate e, 0.110 g, 0.40 mmol), and 1,2-oxazolidin-2-ium chloride (0.055 g, 0.50 mmol), [2-(3-fluorophenyl)-4-methoxy-1,3-thiazol-5-yl](1,2-oxazolidin-2-yl)methanone was prepared as described for intermediate f. The compound was deprotected with 3 equivalents of boron tribromide 1M in dichloromethane, and then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 7:3 as eluent) to obtain the [2-(3-fluorophenyl)-4-hydroxy-1,3-thiazol-5-yl](1,2-oxazolidin-2-yl)methanone as a pale brown solid (0.055 g, Y=47% over two steps).
1H-NMR (CDCl$_3$): δ 11.93 (s, 1H), 7.80-7.73 (m, 2H), 7.44-7.39 (m, 1H), 7.19-7.17 (m, 1H), 4.12-4.08 (t, 2H), 3.94-3.89 (t, 2H), 2.47-2.40 (m, 2H).
MS (ES1+) m/z: 294.99 [M+H]+.

Example 2

Synthesis of [4-hydroxy-2-(2-hydroxyphenyl)-1,3-thiazol-5-yl](1,2-oxazolidin-2-yl)methanone (2)

Starting from 4-methoxy-2-(2-methoxyphenyl)-1,3-thiazole-5-carbonyl chloride (intermediate g, 0.115 g, 0.40 mmol) and 1,2-oxazolidin-2-ium chloride (0.055 g, 0.50 mmol), [4-methoxy-2-(2-methoxyphenyl)-1,3-thiazol-5-yl](1,2-oxazolidin-2-yl)methanone was prepared as described for intermediate f. The compound was deprotected with 4 equivalents of boron tribromide 1M in dichloromethane, and then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane: ethyl acetate 1:1 as eluent) to obtain the [4-hydroxy-2-(2-hydroxyphenyl)-1,3-thiazol-5-yl](1,2-oxazolidin-2-yl)methanone as a pale brown solid (0.054 g, Y=46% over two steps).

$^1$H-NMR (CDCl$_3$): δ 12.14 (br, 1H), 11.65 (s, 1H), 7.66-7.64 (d, 1H), 7.37-7.35 (t, 1H), 7.06-7.04 (d, 1H), 6.91-6.88 (t, 1H), 4.12-4.09 (t, 2H), 3.94-3.92 (t, 2H), 2.48-2.41 (m, 2H).

MS (ES1+) m/z: 293.01 [M+H]+.

Example 3

Synthesis of [2-(3-fluorophenyl)-4-hydroxy-1,3-thiazol-5-yl](1,3-oxazolidin-3-yl)methanone (3)

Starting from 2-(3-fluorophenyl)-4-methoxy-1,3-thiazole-5-carbonyl chloride (intermediate e, 0.110 g, 0.40 mmol) and 1,3-oxazolidin-3-ium chloride (0.055 g, 0.50 mmol), [2-(3-fluorophenyl)-4-methoxy-1,3-thiazol-5-yl](1,3-oxazolidin-3-yl)methanone was prepared as described for intermediate f. The compound was deprotected with 3 equivalents of boron tribromide 1M in dichloromethane, and then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane: ethyl acetate 7:3 as eluent) to obtain the [2-(3-fluorophenyl)-4-hydroxy-1,3-thiazol-5-yl](1,3-oxazolidin-3-yl)methanone as a yellow solid (0.049 g, Y=42% over two steps).

1H-NMR (CDCl$_3$): δ 11.91 (s, 1H), 7.81-7.73 (m, 2H), 7.42-7.37 (m, 1H), 7.15-7.10 (m, 1H), 4.36 (s, 2H), 4.10-4.05 (m, 2H), 3.93-3.89 (m, 2H).

MS (ES1+) m/z: 295.09 [M+H]+.

Example 4

Synthesis of [4-hydroxy-2-(2-hydroxyphenyl)-1,3-thiazol-5-yl](1,3-oxazolidin-3-yl)methanone (4)

Starting from 4-methoxy-2-(2-methoxyphenyl)-1,3-thiazole-5-carbonyl chloride (intermediate g, 0.115 g, 0.40 mmol) and 1,3-oxazolidin-3-ium chloride (0.055 g, 0.50 mmol), [4-methoxy-2-(2-methoxyphenyl)-1,3-thiazol-5-yl](1,3-oxazolidin-3-yl)methanone was prepared as described for intermediate f. The compound was deprotected with 4 equivalents of boron tribromide 1M in dichloromethane, and then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane: ethyl acetate 1:1 as eluent) to obtain the [4-hydroxy-2-(2-hydroxyphenyl)-1,3-thiazol-5-yl](1,3-oxazolidin-3-yl)methanone as a pale brown solid (0.049 g, Y=42% over two steps).

1H-NMR (CDCl$_3$): δ 12.11 (br, 1H), 11.62 (s, 1H), 7.61-7.58 (d, 1H), 7.37-7.35 (t, 1H), 7.05-7.04 (d, 1H), 6.93-6.89 (t, 1H), 4.33 (s, 2H), 4.12-4.09 (m, 2H), 3.94-3.92 (m, 2H).

MS (ES1+) m/z: 293.26 [M+H]+.

Example 5

Synthesis of [2-(3-fluorophenyl)-4-hydroxy-1,3-thiazol-5-yl](oxolan-2-yl)methanone (5)

To a solution of tetrahydro-2-furoic acid (0.135 mL, 1.4 mmol) in dry dioxane (2' mL), 1,1-carbonyldiimidazole (CDI, 0.454 g, 2.8 mmol) was added and the solution was stirred at room temperature for 3 h. Simultaneously, to a solution of 0.209 g (1 mmol) of 2-(3-fluorophenyl)-4-methoxy-1,3-thiazole (intermediate h) in 2 mL of dry dioxane, 0.296 g (4 mmol) of Ca(OH)$_2$ were added and the resulting slurry solution was stirred at room temperature for 30 minutes. To this solution, the solution of activated tetrahydro-2-furoic acid was added and the resulting mixture was heated at 100° C. for 3 h. The reaction was diluted with water (10 mL) and extracted with ethyl acetate (10 mL×2). The organic layer was separated and anhydrified over anhydrous sodium sulphate, the solvent was distilled and the crude purified over silica gel (dichloromethane:methanol 98:2 as eluent) to afford [2-(3-fluorophenyl)-4-methoxy-1,3-thiazol-5-yl](oxolan-2-yl)methanone as light oil (0.117 g, Y=38%). The latter was deprotected with 3 equivalents of boron tribromide 1M in dichloromethane, and then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (dichloromethane: methanol 95:5 as eluent) to obtain the [2-(3-fluorophenyl)-4-hydroxy-1,3-thiazol-5-yl](oxolan-2-yl)methanone as light oil (0.088 g, Y=79%).

1H-NMR (CDCl$_3$): δ 11.90 (s, 1H), 7.81-7.73 (m, 2H), 7.45-7.40 (m, 1H), 7.18-7.16 (m, 1H), 4.56-4.52 (m, 1H), 4.12-4.08 (m, 2H), 3.91-3.88 (m, 2H, 2.47-2.41 (m, 2H).

MS (ES1+) m/z: 294.33 [M+H]+.

Example 6

Synthesis of [4-hydroxy-2-(2-hydroxyphenyl)-1,3-thiazol-5-yl](oxolan-2-yl)methanone (6)

[4-hydroxy-2-(2-hydroxyphenyl)-1,3-thiazol-5-yl](oxolan-2-yl)methanone was synthesized following the procedure described for compound 5 starting from 4-methoxy-2-(2-methoxyphenyl)-1,3-thiazole (intermediate h). The compound was obtained as brown oil (0.054 g, Y=33% over two steps).

1H-NMR (CDCl$_3$): δ 12.10 (br, 1H), 11.66 (s, 1H), 7.65-7.64 (d, 1H), 7.36-7.35 (t, 1H), 7.07-7.04 (d, 1H), 6.91-6.87 (t, 1H), 4.55-4.52 (m, 1H), 4.13-4.10 (m, 2H), 3.92-3.90 (m, 2H), 2.51-2.48 (m, 2H).

MS (ES1+) m/z: 292.29 [M+H]+.

Example 7

Synthesis of [2-(3-fluorophenyl)-4-hydroxy-1,3-thiazol-5-yl](pyrrolidin-1-yl)methanone (7)

Starting from 2-(3-fluorophenyl)-4-methoxy-1,3-thiazole-5-carbonyl chloride (intermediate e, 0.100 g, 0.37 mmol) and pyrrolidine (0.046 mL, 0.55 mmol), [2-(3-fluorophenyl)-4-methoxy-1,3-thiazol-5-yl](pyrrolidin-1-yl)methanone was prepared as described for intermediate f. The compound was deprotected with 3 equivalents of boron tribromide 1M in dichloromethane then stifled overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 9:1 as eluent) to obtain the [2-(3-fluorophenyl)-4-hydroxy-1,3-thiazol-5-yl](pyrrolidin-1-yl)methanone as orange oil (0.066 g, Y=61% over two steps).

1H-NMR (CDCl$_3$): δ 11.91 (s, 1H), 7.80-7.71 (m, 2H), 7.44-7.41 (m, 1H), 7.19-7.18 (m, 1H), 3.56-3.52 (m, 2H), 3.51-3.48 (m, 2H), 2.51-2.48 (m, 2H), 2.46-2.41 (m, 2H).

MS (ES1+) m/z: 292.99 [M+H]+.

Example 8

Synthesis of [4-hydroxy-2-(2-hydroxyphenyl)-1,3-thiazol-5-yl](1,2-oxazinan-2-yl)methanone (8)

Starting from 4-methoxy-2-(2-methoxyphenyl)-1,3-thiazole-5-carbonyl chloride (intermediate g, 0.105 g, 0.37 mmol) and 1,2-oxazinan-2-ium chloride (0.061 g, 0.50 mmol), [4-methoxy-2-(2-methoxyphenyl)-1,3-thiazol-5-yl](1,2-oxazinan-2-yl)methanone was prepared as described for intermediate f. The compound was deprotected with 4 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 1:1 as eluent) to obtain the [4-hydroxy-2-(2-hydroxyphenyl)-1,3-thiazol-5-yl](1,2-oxazinan-2-yl)methanone as a waxy solid (0.039 g, Y=34% over two steps).

1H-NMR (CDCl$_1$): δ 12.33 (br, 1H), 11.62 (s, 1H), 7.65-7.63 (m, 1H), 7.37-7.34 (m, 1H), 7.07-7.05 (m, H), 6.91-6.87 (m, 1H), 4.13-4.11 (t, 2H), 3.96-3.93 (t, 2H), 1.97-1.94 (m, 2H), 1.87-1.82 (m, 2H).

MS (ES1+) m/z: 307.04 [M+H]+.

Example 9

Synthesis of [2-(3-fluorophenyl)-4-hydroxy-1,3-thiazol-5-yl](1,2-oxazinan-2-yl)methanone (9)

Starting from 2-(3-fluorophenyl)-4-methoxy-1,3-thiazole-5-carbonyl chloride (intermediate e, 0.110 g, 0.40 mmol) and 1,2-oxazinan-2-ium chloride (0.062 g, 0.50 mmol), [2-(3-fluorophenyl)-4-methoxy-1,3-thiazol-5-yl](1,2-oxazinan-2-yl)methanone was prepared as described for intermediate f. The compound was deprotected with 3 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 7.3 as eluent) to obtain the [2-(3-fluorophenyl)-4-hydroxy-1,3-thiazol-5-yl](1,2-oxazinan-2-yl)methanone as a orange solid (0.060 g, Y=49% over two steps.

1H-NMR (CD$_3$OD): δ 7.81-7.80 (m, 1H), 7.79-7.75 (m, 1H), 7.52-7.50 (m, 1H), 7.28-7.27 (m, 1H), 4.16-4.13 (t, 2H), 3.94-3.91 (t, 2H), 1.96-1.93 (m, 2H), 1.85-1.81 (m, 2H).

MS (ES1+) m/z: 309.26 [M+H]+.

Example 10

Synthesis of [2-(3-fluorophenyl)-4-hydroxy-1,3-thiazol-5-yl](1,3-oxazinan-3-yl)methanone (10)

Starting from 2-(3-fluorophenyl)-4-methoxy-1,3-thiazole-5-carbonyl chloride (intermediate e, 0.110 g, 0.40 mmol) and 1,3-oxazinan-3-ium chloride (0.061 g, 0.50 mmol), [2-(3-fluorophenyl)-4-methoxy-1,3-thiazol-5-yl](1,3-oxazinan-3-yl)methanone was prepared as described for intermediate f. The compound was deprotected with 3 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 8:2 as eluent) to obtain the [2-(3-fluorophenyl)-4-hydroxy-1,3-thiazol-5-yl](1,3-oxazinan-3-yl)methanone as a orange solid (0.063 g, Y=51% over two steps).

1H-NMR (CD$_3$OD): δ 7.80-7.75 (m, 2H), 7.51-7.49 (m, 1H), 7.28-7.26 (m, 1H), 4.34 (s, 2H), 4.15-4.13 (M, 2H), 3.94-3.90 (m, 2H), 1.95-1.91 (m, 2H).

MS (ES1+) m/z: 309.31 [M+H]+.

Example 11

Synthesis of [4-hydroxy-2-(2-hydroxyphenyl)-1,3-thiazol-5-yl](1,3-oxazinan-3-yl)methanone (11)

Starting from 4-methoxy-2-(2-methoxyphenyl)-1,3-thiazole-5-carbonyl chloride (intermediate g, 0.105 g, 0.37 mmol) and 1,3-oxazinan-3-ium chloride (0.061 g, 0.50 mmol), [4-methoxy-2-(2-methoxyphenyl)-1,3-thiazol-5-yl](1,3-oxazinan-3-yl)methanone was prepared as described for intermediate f. The compound was deprotected with 4 equivalents of boron tribromide 1M in dichloromethane then stirred overnight at room temperature. The reaction was diluted with DOM (10 mL) and stirred with water (10 mL) for 10 minutes. The organic layer was separated and anhydrified over anhydrous sodium sulphate, the solvent was distilled and the crude purified over silica gel (n-hexane:ethyl acetate 1:1 as eluent) to obtain the [4-hydroxy-2-(2-hydroxyphenyl)-1,3-thiazol-5-yl](1,3-oxazinan-3-yl)methanone as a waxy solid (0.043 g, Y=38% over two steps).

1H-NMR (CD$_3$OD): δ 7.81-7.73 (m, 2H), 7.50-7.48 (m, 1H), 7.29-7.28 (m 1H), 4.35 (s, 2H), 4.16-4.15 (m, 2H), 3.95-3.93 (m, 2H), 1.92-1.90 (m, 2H).

MS (ES1+) m/z: 307.14 [M+H]+.

Example 12

Synthesis of [2-(3-fluorophenyl)-4-hydroxy-1,3-thiazol-5-yl](morpholin-4-yl)methanone (12)

Starting from 2-(3-fluorophenyl)-4-methoxy-1,3-thiazole-5-carbonyl chloride (intermediate e, 0.110 g, 0.40 mmol) and morpholine (0.044 mL, 0.50 mmol), [2-(3-fluorophenyl)-4-methoxy-1,3-thiazol-5-yl](morpholin-4-yl)methanone was prepared as described for intermediate f. The compound was deprotected with 3 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 8:2 as eluent) to obtain the [2-(3-fluorophenyl)-4-hydroxy-1,3-thiazol-5-yl](morpholin-4-yl)methanone as a orange solid (0.063 g, Y=51% over two steps).

1H-NMR (CD$_3$OD): δ 7.81-7.78 (m, 2H), 7.50-7.48 (m, 1H), 7.27-7.25 (m, 1H), 3.80-3.75 (m, 4H), 2.94-2.90 (m, 4H).

MS (ES1+) m/z: 309.18 [M+H]+.

Example 13

Synthesis of [4-hydroxy-2-(2-hydroxyphenyl)-1,3-thiazol-5-yl](morpholin-4-yl)methanone (13)

Starting from 4-methoxy-2-(2-methoxyphenyl)-1,3-thiazole-5-carbonyl chloride (intermediate g, 0.105 g, 0.37 mmol) and morpholin (0.044 mL, 0.50 mmol), [4-methoxy-2-(2-methoxyphenyl)-1,3-thiazol-5-yl](morpholin-4-yl)methanone was prepared as described for intermediate f. The compound was deprotected with 4 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 1:1 as eluent) to obtain the [4-hydroxy-2-(2-hydroxyphenyl)-1,3-thiazol-5-yl](morpholin-4-yl)methanone as a waxy solid (0.043 g, Y=38% over two steps).

1H-NMR (CD$_3$OD): δ 7.80-7.76 (m, 2H), 7.51-7.49 (m, 1H), 7.28-7.25 (m, 1H), 3.81-3.77 (m, 4H), 2.93-2.91 (m, 4H).

MS (ES1+) m/z: 307.14 [M+H]+.

Example 14

Synthesis of [2-(3-fluorophenyl)-4-hydroxy-1,3-thiazol-5-yl](piperidin-1-yl)methanone (14)

Starting from 2-(3-fluorophenyl)-4-methoxy-1,3-thiazole-5-carbonyl chloride (intermediate e, 0.100 g, 0.37 mmol) and piperidine hydrochloride (0.067 g, 0.55 mmol), [2-(3-fluorophenyl)-4-methoxy-1,3-thiazol-5-yl](piperidin-1-yl)methanone was prepared as described for intermediate f. The compound was deprotected with 3 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 9:1 as eluent) to obtain the [2-(3-fluorophenyl)-4-hydroxy-1,3-thiazol-5-yl](piperidin-1-yl)methanone as orange oil (0.065, Y=58% over two steps).

1H-NMR (CDCl$_3$): δ 11.91 (s, 1H), 7.80-7.71 (m, 2H), 7.44-7.40 (m, 1H), 7.19-7.17 (m, 1H), 3.55-3.53 (m, 2H), 3.52-3.50 (m, 2H), 2.21-2.18 (m, 2H), 2.15-2.10 (m, 4H).

MS (ES1+) m/z: 307.41 [M+H]+.

Example 15

Synthesis of [2-(3-fluorophenyl)-4-hydroxy-1,3-thiazol-5-yl](pyrrolidin-2-yl)methanone (15)

[2-(3-fluorophenyl)-4-hydroxy-1,3-thiazol-5-yl](pyrrolidin-2-yl)methanone was synthesized following the procedure described for compound 5 but using the DL-proline. The compound was obtained as light red oil (0.043 g, Y=31% over two steps).

1H-NMR (CDCl$_3$): δ 11.91 (s, 1H), 7.81-7.72 (m, 2H), 7.44-7.43 (m, 1H), 7.18-7.15 (m, 1H), 4.14-4.10 (m, 1H), 3.51-3.47 (m, 2H), 2.26-1.80 (m, 4H).

MS (ES1+) m/z: 293.33 [M+H]+.

Example 16

Synthesis of [2-(3-fluorophenyl)-4-hydroxy-1,3-thiazol-5-yl](1-methylpyrrolidin-2-yl)methanone (16)

[2-(3-fluorophenyl)-4-hydroxy-1,3-thiazol-5-yl](1-methylpyrrolidin-2-yl)methanone was synthesized following the procedure described for compound 5 but using the N-methyl proline. The compound was obtained as orange oil (0.047 g, Y=41% over two steps).

1H-NMR (CDCl$_3$): δ 11.90 (s, 1H), 7.81-7.73 (m, 2H), 7.45-7.43 (m, 1H), 7.18-7.14 (m, 1H), 4.14-4.12 (m, 1H), 3.55-3.43 (m, 5H), 2.29-2.07 (m, 4H).

MS (ES1+) m/z: 307.36 [M+H]+.

Example 17

Synthesis of [2-(3-fluorophenyl)-4-hydroxy-1,3-thiazol-5-yl](1H-pyrrol-2-yl)methanone (17)

Compound 17 was obtained following the general procedure for Friedel-Crafts Acylation starting from 2-(3-fluorophenyl)-4-methoxy-1,3-thiazole-5-carbonyl chloride (0.145 g, 0.53 mmol) and pyrrole (0.055 mL, 0.79 mmol). The deprotection of methoxy group was performed with 3 equivalents of boron tribromide 1M in dichloromethane as described for compound 1 and [2-(3-fluorophenyl)-4-hydroxy-1,3-thiazol-5-yl](1H-pyrrol-2-yl)methanone was obtained as brown solid (0.088 g, Y=58%).

1H-NMR (CD$_3$OD): δ 7.85-7.70 (m, 2H), 7.45-7.35 (m, 1H), 7.25-7.19 (m, 1H), 7.05-7.00 (m, 1H), 6.85-6.83 (m, 1H), 6.23-6.22 (m, 1H).

MS (ES1+) m/z: 289.03 [M+H]+.

Example 18

Synthesis of [2-(3-fluorophenyl)-4-hydroxy-1,3-thiazol-5-yl](1-methyl-1H-pyrrol-2-yl)methanone (18)

Compound 18 was obtained following the general procedure for Friedel-Crafts Acylation starting from 2-(3-fluorophenyl)-4-methoxy-1,3-thiazole-5-carbonyl chloride (0.145 g, 0.53 mmol) and N-methyl pyrrole (0.070 mL, 0.79 mmol). The deprotection of methoxy group was performed with 3 equivalents of boron tribromide 1M in dichloromethane as described for compound 1 and [2-(3-fluorophenyl)-4-hydroxy-1,3-thiazol-5-yl](1-methyl-1H-pyrrol-2-yl)methanone was obtained as yellow oil (0.109 g, Y=68%).

1H-NMR (CD$_3$OD) δ 7.83-7.74 (m, 2H), 7.45-7.33 (m, 1H), 7.23-7.20 (m, 1H), 7.03-7.01 (m, 1H), 6.82-6.81 (m, 1H), 6.20-6.19 (m, 1H), 3.8 (s, 3H).

MS (ES1+) m/z: 303.43 [M+H]+.

Example 19

Synthesis of [2-(3-fluorophenyl)-4-hydroxy-1,3-thiazol-5-yl](furan-2-yl)methanone (19)

Compound 19 was obtained following the general procedure for Friedel-Crafts Acylation starting from 2-(3-fluorophenyl)-4-methoxy-1,3-thiazole-5-carbonyl chloride (0.145 g, 0.53 mmol) and furan (0.058 mL, 0.79 mmol). The deprotection of methoxy group was performed with 3 equivalents of boron tribromide 1M in dichloromethane as described for compound 1 and [2-(3-fluorophenyl)-4-hydroxy-1,3-thiazol-5-yl](furan-2-yl)methanone was obtained as light green solid (0.079 g, Y=52%).

1H-NMR (CD$_3$OD): δ 7.81-7.62 (m, 3H), 7.41-7.39 (m, 1H), 7.25-7.10 (m, 2H), 6.82-6.80 (m, 1H).

MS (ES1+) m/z: 290.31 [M+H]+.

Example 20

Synthesis of [2-(3-fluorophenyl)-4-hydroxy-1,3-thiazol-5-yl](thiophen-2-yl)methanone (20)

Compound 20 was obtained following the general procedure for Friedel-Crafts Acylation starting from 2-(3-fluorophenyl)-4-methoxy-1,3-thiazole-5-carbonyl chloride (0.145 g, 0.53 mmol) and thiophene (0.063 mL, 0.79 mmol). The deprotection of methoxy group was performed with 3 equivalents of boron tribromide 1M in dichloromethane as described for compound 1 and [2-(3-fluorophenyl)-4-hydroxy-1,3-thiazol-5-yl](thiophen-2-yl)methanone was obtained as brown solid (0.079 g, Y=49%).

1H-NMR (CD$_3$OD): δ 7.80-7.79 (m, 1H), 7.77-7.69 (m, 2H), 7.40-7.38 (m, 1H), 7.23-7.20 (m, 2H), 6.83-6.81 (m, 1H).

MS (ES1+) m/z: 306.23 [M+H]+.

Example 21

Synthesis of [2-(3-fluorophenyl)-4-hydroxy-1,3-thiazol-5-yl](1H-pyrrol-1-yl)methanone (21)

To a solution of pyrrole (0.066 mL, 0.95 mmol) and NaH (0.025 g, 1.05 mmol) in 4 mL of dry DMF, 2-(3-fluorophenyl)-4-methoxy-1,3-thiazole-5-carbonyl chloride (0.171 g, 0.63 mmol) dissolved in 3 mL of dry DMF was added drop wise. The resulting mixture was then stirred at room temperature overnight. The mixture was quenched with saturated solution NH$_4$Cl (10 mL) and extracted with ethyl acetate (10 mL×2). The organic layer was separated and anhydrified over anhydrous sodium sulphate, the solvent was distilled and the crude purified over silica gel (n-hexane:ethyl acetate 9:1 as eluent) to obtain [2-(3-fluorophenyl)-4-methoxy-1,3-thiazol-5-yl](1H-pyrrol-1-yl)methanone (0.157 g, 0.52 mmol, Y=82%). The latter was deprotected with 3 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (n-hexane:ethyl acetate 8:2 as eluent) to obtain the [2-(3-fluorophenyl)-4-hydroxy-1,3-thiazol-5-yl](1H-pyrrol-1-yl)methanone as light oil (0.132 g, Y=88%).

1H-NMR (CD$_3$OD): δ 7.85-7.70 (m, 2H), 7.45-7.35 (m, 1H), 7.25-7.19 (m, 2H), 7.05-7.00 (m, 1H), 6.85-6.83 (m, 2H).

MS (ES1+) m/z: 289.41 [M+H]+.

Example 22

Synthesis of [2-(3-fluorophenyl)-4-hydroxy-1,3-thiazol-5-yl](pyridin-2-yl)methanone (22)

A 10 mL round-bottomed flask equipped with a magnetic stirrer was charged with 2-(3-fluorophenyl)-4-methoxy-1,3-thiazole-6-carbonyl chloride (0.060 g, 0.221 mmol) and 5 mL of dry THF and it was refrigerated to −78° C. The solution was treated at the same temperature with pyridin-2-yl-magnesium bromide 0.25 M in THF (0.88 mL, 0.221 mmol) then stirred at −60° C. for 1 hour. The cooling system was removed and the reaction quenched at room temperature with saturated aqueous ammonium chloride solution (10 mL). The mixture was extracted with ethyl acetate (10 mL×2), the organics were collected and washed twice with water (10 mL×2) and once with brine (10 mL). The organic phase was then anhydrified and the solvents vacuum removed. The crude was purified over silica gel by flash chromatography to afford [2-(3-fluorophenyl)-4-methoxy-1,3-thiazol-5-yl](pyridin-2-yl)methanone in 54% yield (0.037 g). The latter was deprotected with 3 equivalents of boron tribromide 1M in dichloromethane then stirred overnight at room temperature. The reaction was diluted with DCM (10 mL) and stirred with water (10 mL) for 10 minutes. The organic layer was separated and anhydrified over anhydrous sodium sulphate, the solvent was distilled and the crude purified over silica gel (dichloromethane:methanol 95:5 as eluent) to obtain the [2-(3-fluorophenyl)-4-hydroxy-1,3-thiazol-5-yl](pyridin-2-yl)methanone as light green oil (0.024 g. Y=68%).

1H-NMR (CD$_3$OD): δ 8.80-8.75 (m, 1H), 8.08-8.02 (m, 1H), 7.80-7.71 (m, 3H), 7.54-7.39 (m, 2H), 7.19-7.17 (m, 1H), MS (ES1+) m/z: 301.02 [M+H]+.

Example 23

Synthesis of [2-(3-fluorophenyl)-4-hydroxy-1,3-thiazol-5-yl](pyridin-3-yl)methanone (23)

[2-(3-fluorophenyl)-4-hydroxy-1,3-thiazol-5-yl](pyridin-3-yl)methanone was synthesized according the procedure described for compound 22 and starting from pyridin-3-yl-magnesium chloride. The compound was obtained as orange solid (0.055 g, Y=62%).

1H-NMR (CD$_3$OD): δ 9.1 (s, 1H), 8.81-8.79 (m, 1H), 8.36-8.32 (m, 1H), 7.81-7.73 (m, 2H), 7.64-7.39 (m, 2H), 7.29-7.18 (m, 1H).

MS (ES1+) m/z: 301.03 [M+H]+.

Example 24

Synthesis of [2-(3-fluorophenyl)-4-hydroxy-1,3-thiazol-5-yl](pyridin-4-yl)methanone (24)

[2-(3-fluorophenyl)-4-hydroxy-1,3-thiazol-5-yl](pyridin-4-yl)methanone was synthesized according the procedure described for compound 22 and starting from pyridin-4-yl-magnesium chloride. The compound was obtained as light brown solid (0.046 g, Y=68%).

1H-NMR (CD$_3$OD): δ 9.05-9.03 (m, 2H), 8.71-8.69 (m, 2H), 7.81-7.73 (m, 2H), 7.44-7.39 (m, 1H), 7.19-7.17 (m, 1H).

MS (ES1+) m/z: 301.02 [M+H]+.

Example 25

Synthesis of [2-(3-fluorophenyl)-4-hydroxy-1,3-thiazol-5-yl](1H-imidazol-1-yl)methanone (25)

[2-(3-fluorophenyl)-4-hydroxy-1,3-thiazol-5-yl](1H-imidazol-1-yl)methanone was synthesized according the procedure described for compound 21 and starting from 1H-imidazole. The compound was obtained as brown solid (0.088 g, Y=67%).

1H-NMR (CD$_3$OD): δ 7.79-7.73 (m, 2H), 7.7 (s, 1H), 7.44-7.39 (1H), 7.19-7.17 (m, 1H), 7.03-7.01 (m, 2H).

MS (ES1+) m/z: 290.31 [M+H]+.

Example 26

Synthesis of [2-(3-fluorophenyl)-4-hydroxy-1,3-thiazol-5-yl](1H-pyrazol-1-yl)methanone (26)

[2-(3-fluorophenyl)-4-hydroxy-1,3-thiazol-5-yl](1H-pyrazol-1-yl)methanone was synthesized according the procedure described for compound 21 and starting from 1H-pyrazole. The compound was obtained as brown solid (0.095 g. Y=69%).

1H-NMR (CDCl$_3$): δ 11.91 (s, 1H), 7.80-7.73 (m, 2H), 7.72-7.70 (m, 2H), 7.44-7.39 (m, 1H), 7.19-7.17 (m, 1H), 6.34-6.31 (m, 1H).

MS (ES1+) m/z: 290.35 [M+H]+.

Example 27

Synthesis of [2-(3-fluorophenyl)-4-hydroxy-1,3-thiazol-5-yl](1,2-oxazepan-2-yl)methanone (27)

Starting from 2-(3-fluorophenyl)-4-methoxy-1,3-thiazole-5-carbonyl chloride (intermediate e, 0.110 g, 0.40 mmol) and 12-oxazepam-2-ium chloride (0.069 g, 0.50 mmol), [2-(3-fluorophenyl)-4-hydroxy-1,3-thiazol-5-yl](1,2-oxazepan-2-yl)methanone was synthesized according the procedure described for compound 1. The compound was obtained as yellow solid (0.102 g, Y=79%).

1H-NMR (CDCl$_3$): δ 12.22 (s, 1H), 7.79-7.72 (m, 2H), 7.44-7.39 (m, 1H), 7.19-7.17 (m, 1H), 4.18-4.15 (m, 2H), 3.93-3.89 (m, 2H), 1.92-1.85 (m, 6).

MS (ES1+) m/z: 323.37 [M+H]+.

Example 28

Synthesis of [2-(3-fluorophenyl)-4-hydroxy-1,3-thiazol-5-yl](5-oxa-6-azaspiro[2.4]heptan-6-yl)methanone (28)

Starting from 2-(3-fluorophenyl)-4-methoxy-1,3-thiazole-5-carbonyl chloride (intermediate e, 0.100 g, 0.37 mmol) and 5-oxa-6-azaspiro[2.4]heptane (0.039 g, 0.40 mmol), [2-(3-fluorophenyl)-4-hydroxy-1,3-thiazol-5-yl](5-oxa-6-azaspiro[2.4]hepten-6-yl)methanone was synthesized according the procedure described for compound 1. The compound was obtained as yellow solid (0.084 g, Y=71%).

1H-NMR (CDCl$_3$) δ 11.92 (s, 1H), 7.79-7.73 (m, 2H), 7.43-7.40 (m, 1H), 7.17-7.16 (m, 1H), 3.81-3.73 (m, 2H), 3.68-3.59 (m, 2H), 1.92-1.86 (m, 4H).

MS (ES1+) m/z: 321.35 [M+H]+.

Example 29

Synthesis of [2-(3-fluorophenyl)-4-hydroxy-1,3-thiazol-5-yl](5-methyl-1,2-oxazolidin-2-yl) methanone (29)

Starting from 2-(3-fluorophenyl)-4-methoxy-1,3-thiazole-5-carbonyl chloride (intermediate e, 0.100 g, 0.37 mmol) and 5-methyl-1,2-oxazolidine (0.035 g, 0.40 mmol), [2-(3-fluorophenyl)-4-hydroxy-1,3-thiazol-5-yl](5-methyl-1,2-oxazolidin-2-yl)methanone was synthesized according the procedure described for compound 1. The compound was obtained as yellow solid (0.083 g, Y=73%).

1H-NMR (CDCl$_3$): δ 1190 (s, 1H), 7.79-7.74 (m, 2H), 7.44-7.38 (m, 1H), 7.16-7.11 (m, 1H), 3.68-3.58 (m, 2H), 3.48-3.39 (m, 1H), 2.47-2.23 (m, 2H), 1.87 (d, 3H).

MS (ES1+) m/z: 309.31 [M+H]+.

Example 30

Synthesis of [2-(3-fluorophenyl)-4-hydroxy-1,3-thiazol-5-yl](hexahydro-2H-cyclopenta[d][1,2]oxazol-2-yl)methanone (30)

Starting from 2-(3-fluorophenyl)-4-methoxy-1,3-thiazole-5-carbonyl chloride (intermediate e, 0.100 g, 0.37 mmol) and hexahydro-2H-cyclopenta[d][1,2]oxazole (0.047 g, 0.42 mmol), [2-(3-fluorophenyl)-4-hydroxy-1,3-thiazol-5-yl](hexahydro-2H-cyclopenta[d][1,2]oxazol-2-yl)methanone was synthesized according the procedure described for compound 1. The compound was obtained as yellow solid (0.094 g, Y=67%).

1H-NMR (CDCl$_3$): δ 11.97 (s, 1H), 7.80-7.75 (m, 2H), 7.43-7.36 (m, 1H), 7.15-7.12 (m, 1H), 3.90-3.81 (m, 1H), 3.71-3.66 (m, 2H), 2.98-2.79 (m, 1H), 1.87-1.81 (m, 2H), 1.67-1.41 (m, 4H).

MS (ES1+) m/z: 335.35 [M+H]+.

Example 31

Synthesis of [2-(3-fluorophenyl)-4-hydroxy-1,3-thiazol-5-yl](1H-1,2,3-triazol-1-yl)methanone (31)

Starting from 2-(3-fluorophenyl)-4-methoxy-1,3-thiazole-5-carbonyl chloride (intermediate e, 0.120 g, 0.44 mmol) and 1H-1,2,3-triazole (0.035 g, 0.50 mmol), [2-(3-fluorophenyl)-4-hydroxy-1,3-thiazol-5-yl]4-(1H-1,2,3-triazol-1-yl)methanone was synthesized according the procedure described for compound 1. The compound was obtained as brown solid (0.088 g, Y=69%).

1H-NMR (CDCl$_3$): δ 11.77 (s, 1H), 7.67-7.61 (m, 2H), 7.55 (d, 1H), 7.40-7.32 (m, 1H), 7.17 (d, 1H), 7.07-7.02 (m, 1H).

MS (ES1+) m/z: 291.27 [M+H]+.

Example 32

Synthesis of [2-(3-fluorophenyl)-4-hydroxy-1,3-thiazol-5-yl](1-methyl-1H-tetrazol-5-yl)methanone (32)

At room temperature, 0.230 g of 2-(3-fluorophenyl)-4-methoxy-1,3-thiazole-5-carbonyl chloride (0.84 mmol) were admixed with 0.035 g (0.84 mmol) of methyl isocyanide. The mixture was then heated at 60° C. for 3 hours. The mixture was admixed with 5 ml of acetonitrile and cooled to 0° C. The reaction mixture was added to 0.055 g of sodium azide (0.84 mmol) in 0.105 ml of 2,6-dimethylpyridine (0.90 mmol) in 5 ml of acetonitrile at 0° C. The mixture was then heated to 60° C. and stirred at this temperature for 1 hour. At room temperature, 10 ml of water and 10 ml of ethyl acetate were added to the mixture. The organic phase was separated off and the aqueous phase was extracted with 10 ml of ethyl acetate. The combined organic phases were dried over anhydrous sodium sulphate and the solvent was removed in vacuo. The crude was purified over silica gel (dichloromethane:methanol 95:5 as eluent) to obtain [2-(3-fluorophenyl)-

4-methoxy-1,3-thiazol-5-yl](1-methyl-1H-tetrazol-5-yl)
methanone in a yield of 82% as brown powder. [2-(3-
fluorophenyl)-4-methoxy-1,3-thiazol-5-yl](1-methyl-1H-
tetrazol-5-yl)methanone was deprotected with 3 equivalents
of boron tribromide 1M in dichloromethane, and then stirred
overnight at room temperature. The reaction was diluted
with DCM (10 mL) and stirred with water (10 mL) for 10
minutes. The organic layer was separated and anhydrified
over anhydrous sodium sulphate, the solvent was distilled
and the crude purified over silica gel (dichloromethane:
methanol 90:10 as eluent) to obtain [2-(3-fluorophenyl)-4-
hydroxy-1,3-thiazol-5-yl](1-methyl-1H-tetrazol-5-yl)
methanone as a yellow powder (0.122 g, 47% yield over two
steps).

1H-NMR (CDCl$_3$): δ 11.80 (s, 1H), 7.77-7.71 (m, 2H), 7.61-7.52 (m, 1H), 7.47-7.42 (m, 1H), 4.23 (s, 3H).

MS (ES1+) m/z: 306.28 [M+H]+.

Example 33

In Vitro TRPM8 Assay

The TRPM8 antagonistic activity of all 26 compounds was determined by measuring changes in intracellular calcium levels using a $Ca^{+2}$ sensitive fluorescent dye. The experiments were performed using HEK-293 cells stably expressing the human TRPM8. Cells were seeded 10000 cells/well in 384 plates coated by Poly-D-Lysine MATRIX black/clear bottom (Thermo Scientific, Waltham, Mass. USA) in complete medium and grown overnight at 37° C., 5% $CO_2$. 24 h after seeding, cell culture media was removed, cells were washed with Tyrode's assay buffer and then loaded with the fluorescent $Ca^{+2}$ indicator Fluo-4 NW dye (Molecular Probes, Life Technologies, Paisley, UK) supplemented with water-soluble Probenecid (Molecular Probes). Dye loaded cell plates were incubated for 1 h at room temperature. The compounds or vehicle were added and the kinetic response was monitored by a fluorimetric imaging plate (FLIPRTETRA; Molecular Devices, Sunnyvale, Calif., USA) over a period of five minutes (300 seconds). A second injection 5 minutes later of the reference agonist Cooling Agent 10 or Icilin at EC80 concentration was performed. The signal of the emitted fluorescence was recorded during additional three minutes. Data were analyzed by Spotfire DecisionSite version 9.1.1. The bioactivity exerted by the compounds or vehicle was expressed as a percent inhibition and IC50 values were then calculated. The percentage scale is defined by a 100% inhibition in which the Relative Fluorescence Units (RFUs) of the test were identical to the MIN controls in second injection (Capsazepine at IC100, 50 µM) and 0% of inhibition in which the RFUs of the test were identical to the MAX controls in second injection (Cooling Agent 10 at EC80, 20-30 µM). The results obtained with each compound tested are reported in Table 1.

Example 34

In Vitro Cold Stimulation Assay

The TRPM8 antagonisticic activity of all 26 compounds was determined in an in vitro cold stimulation assay.

In details, HEK-293 cells stably expressing with the human TRPM8 were seeded (1.5-1.8×106) in a T75 flask in complete medium. 3-4 days after seeding (~80% confluent cells), the medium was removed and cells were loaded by a solution of Screen Quest™ Fluo-8 NW dye (ABS Bioquest,
Sunnyvale, Calif., USA) in the dark. Dye-loaded cell flasks were incubated for 45 minutes at room temperature in the dark and the Fluo-8 NW solution was then removed and cells were seeded in the 96 Assay Plates (MicroAmp™ Optical 96-Well Reaction Plates; Applied Biosystems, Life technologies) at 100,000 cells/'well (20 µl/well). Each compound 1-26 was added and incubated at room temperature for 5 minutes. The signal was recorded for 2 minutes at 25° C. and then the temperature was lowered to sub-physiological levels (14° C.) and signal recorded for 3 minutes by the ABI Prism® 7900HT Sequence Detection System (Life Technologies). The fluorescence difference (ΔF=fluorescence at 525 nm at 14° C.–fluorescence at 525 nm at 25° C.) was assessed. The analysis was performed computing ΔF/F0, where F0 was the fluorescent signal at the starting temperature (25° C.) IC50 (half maximal concentration) curves were generated by fitting the fluorescence data with a sigmoidal curve equation using GraphPad PRISM® software (version 5, GraphPad Software Inc., La Jolla, Calif., USA). All data point determinations were performed in duplicate before a mean value was calculated, including error bars representing the standard error of the mean. The results obtained with each compound tested are reported in Table 1.

Example 35

Metabolic Stability in Rat Microsomes
Phase I Assay Protocol

Compounds 1, 2, 8 and 9 in duplicate were dissolved in DMSO and pre-incubated, at the final concentration of 1 µM, for 10 min at 37° C. in potassium phosphate buffer 50 mM pH 7.4, 3 mM MgCl2, with rat liver microsomes (Xenotech) at the final concentration of 0.5 mg/ml.

After the pre-incubation period, reactions were started by adding the cofactors mixture (NADP, Glc6P, Glc6P-DH in 2% Sodium bicarbonte); samples (50 µl) were taken at time 0, 10, 20, 30 and 60 min added to 150 µl of acetonitrile with Verapamil 0.02 µM as Internal Standard (IS) to stop the reaction. After centrifugation the supernatants were analysed by LC-MS/MS.

A control sample without cofactors was added in order to check the stability of test compounds in the matrix after 60 min. 7-Ethoxycoumarin and propranolol were added as reference standards. The result obtained with each compound is reported in Table 1.

Phase II Assay Protocol

Rat liver microsomes (0.5 mg/mL final conc.) were incubated in ice for 15 min in 50 mM potassium phosphate buffer pH 7.4, 3 mM $MgCl_2$ and activated with Alamethicin 50 µg/mg microsomal protein. Samples were transferred at 37° C. and compounds 1, 2, 8 and 9, dissolved in DMSO, were added in duplicate at the final concentration of 1 µM. After 5 min, reaction is started by adding 25 µl of UDPGA (16.15 mg/ml in 0.2% Sodium Bicarbonate). Samples were taken at time 0, 10, 20, 30 and 60 min added to 150 µl of acetonitrile with Verapamil 0.02 uM as Internal Standard (IS) to stop the reaction. After centrifugation the supernatants were analysed by LC-MS/MS. 7-Hydroxycoumarin was added as reference standard. The result obtained with each compound is reported in Table 1.

TABLE 1

| Example No | Structure | Name | Ca²⁺ (IC$_{50}$ μM) Icilin | Ca²⁺ (IC$_{50}$ μM) Cool 10 | COLD IC$_{50}$ μM | Metabolic Stability (t$_{1/2}$, min) Phase1 | Metabolic Stability (t$_{1/2}$, min) Phase2 |
|---|---|---|---|---|---|---|---|
| 1 | 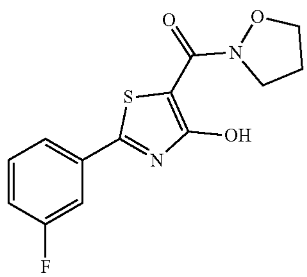 [SMILES: O=C(c1sc(-c2cccc(F)c2)nc1O)N1CCCO1] | [2-(3-fluorophenyl)-4-hydroxy-1,3-thiazol-5-yl](1,2-oxazolidin-2-yl)methanone | 0.017 | 0.016 | 0.0045 | 185 | 120 |
| 2 | 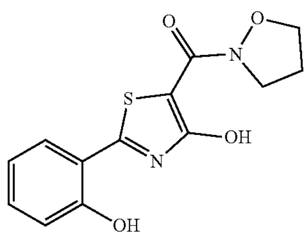 [SMILES: O=C(c1sc(-c2ccccc2O)nc1O)N1CCCO1] | [4-hydroxy-2-(2-hydroxyphenyl)-1,3-thiazol-5-oxazolidin-2-yl)methanone | 0.012 | 0.011 | 0.0055 | 97 | 86 |
| 3 | 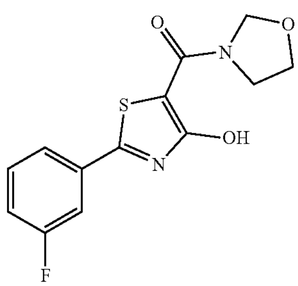 [SMILES: O=C(c1sc(-c2cccc(F)c2)nc1O)N1CCOC1] | [2-(3-fluorophenyl)-4-hydroxy-1,3-thiazol-5-yl](1,3-oxazolidin-3-yl)methanone | 0.112 | 0.115 | 0.043 | 78 | 55 |
| 4 | 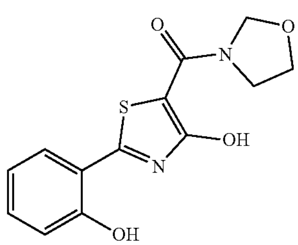 [SMILES: O=C(c1sc(-c2ccccc2O)nc1O)N1CCOC1] | [4-hydroxy-2-(2-hydroxyphenyl)-1,3-thiazol-5-yl](1,3-oxazolidin-3-yl)methanone | 0.122 | 0.104 | 0.039 | 64 | 41 |
| 5 | 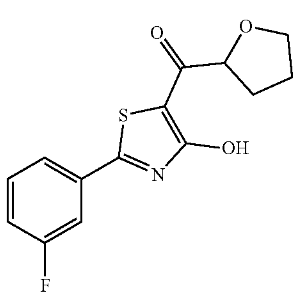 [SMILES: O=C(c1sc(-c2cccc(F)c2)nc1O)C1CCCO1] | [2-(3-fluorophenyl)-4-hydroxy-1,3-thiazol-5-yl](oxolan-2-yl)methanone | 0.362 | 0.326 | 0.124 | 52 | 45 |

TABLE 1-continued

| Example No | Structure | Name | Ca$^{2+}$ (IC$_{50}$ μM) Icilin | Ca$^{2+}$ (IC$_{50}$ μM) Cool 10 | COLD IC$_{50}$ μM | Metabolic Stability (t$_{1/2}$, min) Phase1 | Metabolic Stability (t$_{1/2}$, min) Phase2 |
|---|---|---|---|---|---|---|---|
| 6 | | [4-hydroxy-2-(2-hydroxyphenyl)-1,3-thiazol-5-yl](oxolan-2-yl)methanone | 0.452 | 0.401 | 0.230 | 56 | 33 |
| 7 | | [2-(3-fluorophenyl)-4-hydroxy-1,3-thiazol-5-yl](pyrrolidin-1-yl)methanone | 1.56 | 1.36 | 1.23 | 46 | 51 |
| 8 | | [4-hydroxy-2-(2-hydroxyphenyl)-1,3-thiazol-5-yl](1,2-oxazinan-2-yl)methanone | 0.088 | 0.081 | 0.007 | 102 | 43 |
| 9 | | [2-(3-fluorophenyl)-4-hydroxy-1,3-thiazol-5-yl](1,2-oxazinan-2-yl)methanone | 0.123 | 0.167 | 0.008 | 98 | 51 |
| 10 | | [2-(3-fluorophenyl)-4-hydroxy-1,3-thiazol-5-yl](1,3-oxazinan-3-yl)methanone | 0.231 | 0.256 | 0.102 | 55 | 46 |

TABLE 1-continued

| Example No | Structure | Name | Ca$^{2+}$ (IC$_{50}$ μM) Icilin | Cool 10 | COLD IC$_{50}$ μM | Metabolic Stability (t$_{1/2}$, min) Phase1 | Phase2 |
|---|---|---|---|---|---|---|---|
| 11 | 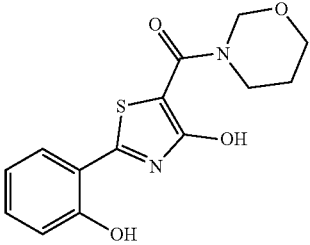 [SMILES: O=C(c1sc(-c2ccccc2O)nc1O)N1CCCOC1] | [4-hydroxy-2-(2-hydroxyphenyl)-1,3-thiazol-5-yl](1,3-oxazinan-3-yl)methanone | 0.256 | 0.281 | 0.106 | 51 | 50 |
| 12 | 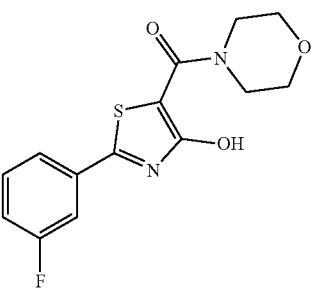 [SMILES: O=C(c1sc(-c2cccc(F)c2)nc1O)N1CCOCC1] | [2-(3-fluorophenyl)-4-hydroxy-1,3-thiazol-5-yl](morpholin-4-yl)methanone | 1.21 | 0.963 | 0.853 | 54 | 32 |
| 13 | 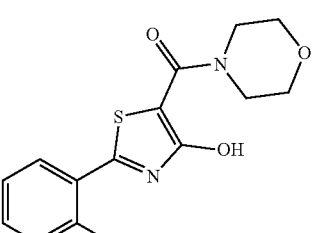 | [4-hydroxy-2-(2-hydroxyphenyl)-1,3-thiazol-5-yl](morpholin-4-yl)methanone | 1.22 | 1.12 | 0.752 | 78 | 36 |
| 14 | 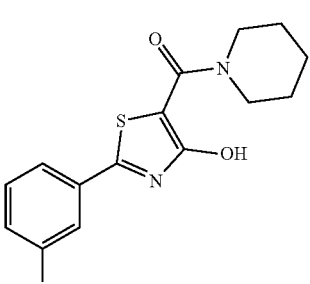 | [2-(3-fluorophenyl)-4-hydroxy-1,3-thiazol-5-yl](piperidin-1-yl)methanone | 1.47 | 1.51 | 0.985 | 67 | 65 |
| 15 | 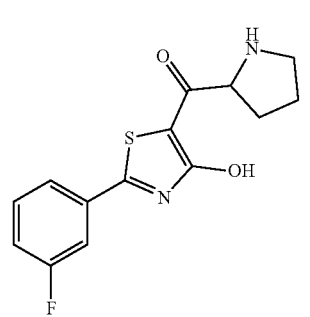 [SMILES: O=C(c1sc(-c2cccc(F)c2)nc1O)C1CCCN1] | [2-(3-fluorophenyl)-4-hydroxy-1,3-thiazol-5-yl](pyrrolidin-2-yl)methanone | 1.23 | 1.56 | 1.31 | 65 | 54 |

TABLE 1-continued

| Example No | Structure | Name | Ca²⁺ (IC$_{50}$ μM) | | COLD IC$_{50}$ μM | Metabolic Stability (t$_{1/2}$, min) | |
|---|---|---|---|---|---|---|---|
| | | | Icilin | Cool 10 | | Phase1 | Phase2 |
| 16 | 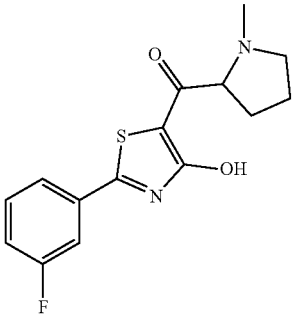 [SMILES: CN1CCCC1C(=O)c1sc(-c2cccc(F)c2)nc1O] | [2-(3-fluorophenyl)-4-hydroxy-1,3-thiazol-5-yl](1-methylpyrrolidin-2-yl)methanone | 1.36 | 1.34 | 1.01 | 32 | 34 |
| 17 | 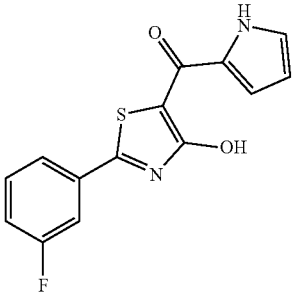 [SMILES: O=C(c1ccc[nH]1)c1sc(-c2cccc(F)c2)nc1O] | [2-(3-fluorophenyl)-4-hydroxy-1,3-thiazol-5-yl](1H-pyrrol-2-yl)methanone | 0.564 | 0.482 | 0.124 | 90 | 82 |
| 18 | 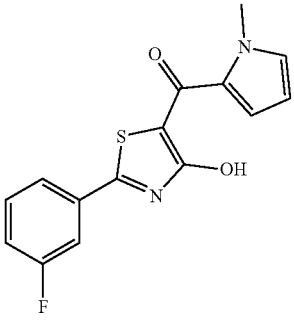 [SMILES: Cn1cccc1C(=O)c1sc(-c2cccc(F)c2)nc1O] | [2-(3-fluorophenyl)-4-hydroxy-1,3-thiazol-5-yl](1-methyl-1H-pyrrol-2-yl)methanone | 1.09 | 1.08 | 1.45 | 78 | 55 |
| 19 | 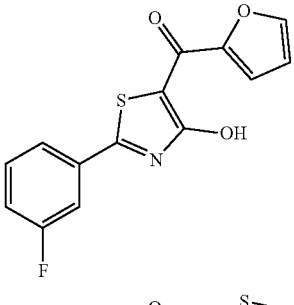 | [2-(3-fluorophenyl)-4-hydroxy-1,3-thiazol-5-yl](furan-2-yl)methanone | 1.15 | 1.17 | 1.78 | 42 | 21 |
| 20 | 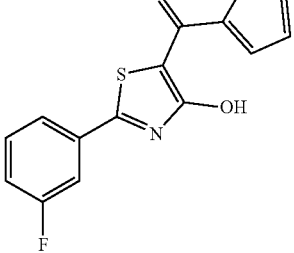 | [2-(3-fluorophenyl)-4-hydroxy-1,3-thiazol-5-yl](thiophen-2-yl)methanone | 1.11 | 0,96 | 1.38 | 68 | 59 |

TABLE 1-continued

| Example No | Structure | Name | Ca$^{2+}$ (IC$_{50}$ μM) | | COLD IC$_{50}$ μM | Metabolic Stability (t$_{1/2}$, min) | |
|---|---|---|---|---|---|---|---|
| | | | Icilin | Cool 10 | | Phase1 | Phase2 |
| 21 | 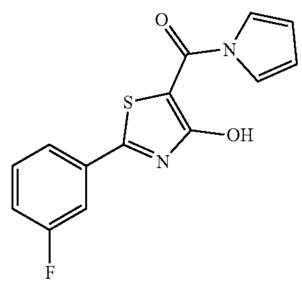 [SMILES: O=C(c1sc(-c2cccc(F)c2)nc1O)n1cccc1] | [2-(3-fluorophenyl)-4-hydroxy-1,3-thiazol-5-yl](1H-pyrrol-1-yl)methanone | 0.745 | 0.651 | 0.657 | 32 | 35 |
| 22 | 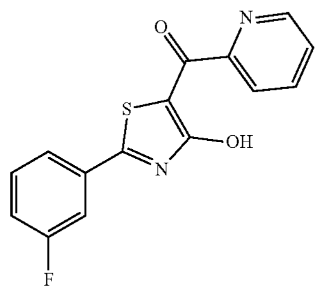 [SMILES: O=C(c1ccccn1)c1sc(-c2cccc(F)c2)nc1O] | [2-(3-fluorophenyl)-4-hydroxy-1,3-thiazol-5-yl](pyridin-2-yl)methanone | 0.540 | 0.523 | 0.478 | 52 | 55 |
| 23 | 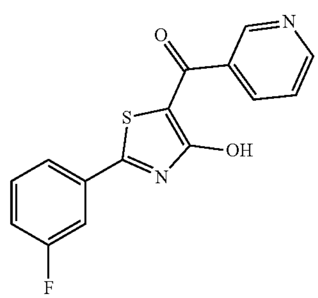 [SMILES: O=C(c1cccnc1)c1sc(-c2cccc(F)c2)nc1O] | [2-(3-fluorophenyl)-4-hydroxy-1,3-thiazol-5-yl](pyridin-3-yl)methanone | 0.695 | 0.621 | 0.578 | 52 | 51 |
| 24 | 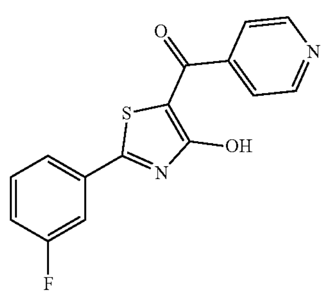 [SMILES: O=C(c1ccncc1)c1sc(-c2cccc(F)c2)nc1O] | [2-(3-fluorophenyl)-4-hydroxy-1,3-thiazol-5-yl](pyridin-4-yl)methanone | 0.624 | 0.601 | 0.525 | 40 | 48 |
| 25 | 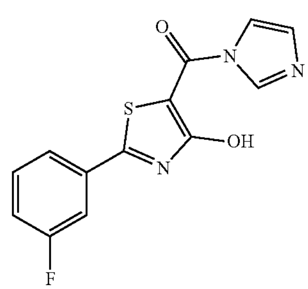 [SMILES: O=C(c1sc(-c2cccc(F)c2)nc1O)n1ccnc1] | [2-(3-fluorophenyl)-4-hydroxy-1,3-thiazol-5-yl](1H-imidazol-1-yl)methanone | 1.247 | 1.253 | 0.972 | 45 | 40 |

TABLE 1-continued

| Example No | Structure | Name | Ca$^{2+}$ (IC$_{50}$ μM) | | COLD IC$_{50}$ μM | Metabolic Stability (t$_{1/2}$, min) | |
|---|---|---|---|---|---|---|---|
| | | | Icilin | Cool 10 | | Phase1 | Phase2 |
| 26 | | [2-(3-fluorophenyl)-4-hydroxy-1,3-thiazol-5-yl](1H-pyrazol-1-yl)methanone | 1.325 | 1.649 | 1.32 | 89 | 86 |
| 27 | | [2-(3-fluorophenyl)-4-hydroxy-1,3-thiazol-5-yl](1,2-oxazepan-2-yl)methanone | 0.143 | 0.121 | 0.046 | 75 | 63 |
| 28 | | [2-(3-fluorophenyl)-4-hydroxy-1,3-thiazol-5-yl](5-oxa-6-azaspiro[2.4]heptan-6-yl)methanone | 0.143 | 0.086 | 0.054 | 73 | 61 |
| 29 | | [2-(3-fluorophenyl)-4-hydroxy-1,3-thiazol-5-yl](5-methyl-1,2-oxazolidin-2-yl)methanone | 0.111 | 0.091 | 0.031 | 91 | 78 |
| 30 | | [2-(3-fluorophenyl)-4-hydroxy-1,3-thiazol-5-yl](hexahydro-2H-cyclopenta[d][1,2]oxazol-2-yl)methanone | 0.087 | 0.084 | 0.069 | 82 | 85 |

TABLE 1-continued

| Example No | Structure | Name | Ca²⁺ (IC₅₀ μM) Icilin | Ca²⁺ (IC₅₀ μM) Cool 10 | COLD IC₅₀ μM | Metabolic Stability (t₁/₂, min) Phase1 | Metabolic Stability (t₁/₂, min) Phase2 |
|---|---|---|---|---|---|---|---|
| 31 | | [2-(3-fluorophenyl)-4-hydroxy-1,3-thiazol-5-yl](1H-1,2,3-triazol-1-yl)methanone | 0.082 | 0.94 | 0.050 | 85 | 67 |
| 32 | 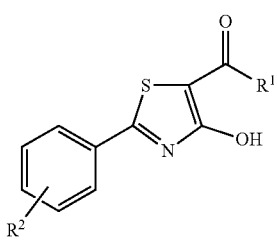 | [2-(3-fluorophenyl)-4-hydroxy-1,3-thiazol-5-yl](1-methyl-1H-tetrazol-5-yl)methanone | 0.101 | 0.098 | 0.063 | 81 | 69 |

The invention claimed is:

1. A compound of formula (I):

$$(I)$$

wherein
$R^1$ is an unsubstituted or substituted 5, 6 or 7-membered, aliphatic or aromatic heterocycle group having 1, 2, 3 or 4 heteroatoms selected from the group consisting of N, O and S; and
$R^2$ is selected from the group consisting of hydrogen, $C_1$-$C_2$ alkyl, F, Cl and OH;
or a pharmaceutically acceptable salt thereof.

2. The compound according to claim 1, wherein $R^1$ is selected from the group consisting of oxazolidinyl, oxolanyl, pyrrolidinyl, oxazinanyl, morpholinyl, piperidinyl, methylpyrrolidinyl, pyrrolyl, methylpyrrolyl, furanyl, thiophenyl, pyridinyl, imidazolyl, pyrazolyl, oxadiazolyl and oxazolyl.

3. The compound according to claim 1, wherein $R^1$ is selected from the group consisting of 1,2-oxazolidin-2-yl, 1,3-oxazolidin-3-yl, oxolan-2-yl, pyrrolidin-1-yl, 1,2-oxazinan-2-yl, 1,3-oxazinan-3-yl, morpholin-4-yl, piperidin-1-yl, pyrrolidin-2-yl, 1-methylpyrrolidin-2-yl, 1H-pyrrol-2-yl, 1-methyl-1H-pyrrol-2-yl, furan-2-yl, thiophen-2-yl, 1H-pyrrol-1-yl, pyridin-2-yl, pyridin-3-yl, pyridin-4-yl, 1H-imidazol-1-yl and 1H-pyrazol-1-yl.

4. The compound according to claim 1, wherein the 5, 6 or 7-membered, aliphatic or aromatic heterocycle is unsubstituted.

5. The compound according to claim 1, wherein the 5, 6 or 7-membered, aliphatic or aromatic heterocycle is substituted with one or more groups independently selected from $C_1$-$C_3$ alkyl, cycloalkyl, Cl and F or the heterocycle is substituted with a saturated cyclic moiety.

6. The compound according to claim 5, wherein the saturated cyclic moiety is cyclobutane, cyclopentane or cyclohexane.

7. The compound according to claim 1, wherein $R^2$ is F or OH.

8. The compound according to claim 7, wherein $R^2$ is 3-F or 2-OH.

9. The compound according to claim 1, wherein
$R^1$ is oxazolidinyl and $R^2$ is F or OH,
or
$R^1$ is oxolanyl and $R^2$ is F or OH,
or
$R^1$ is pyrrolidinyl and $R^2$ is F or OH,
or
$R^1$ is oxazinanyl and $R^2$ is F or OH,
or
$R^1$ is morpholinyl and $R^2$ is F or OH,
or
$R^1$ is piperidinyl and $R^2$ is F or OH,
or
$R^1$ is methylpyrrolidinyl and $R^2$ is F or OH,
or
$R^1$ is pyrrolyl and $R^2$ is F or OH,
or
$R^1$ is methylpyrrolyl and $R^2$ is F or OH,
or
$R^1$ is furanyl and $R^2$ is F or OH,
or R¹ is thiophenyl and R² is F or OH,
or
R¹ is pyridinyl and R² is F or OH,
or
R¹ is imidazolyl and R² is F or OH,
or
R¹ is pyrazolyl and R² is F or OH.

10. The compound according to claim 1, which is selected from the group consisting of:
- [2-(3-fluorophenyl)-4-hydroxy-1,3-thiazol-5-yl](1,2-oxazolidin-2-yl)methanone,
- [4-hydroxy-2-(2-hydroxyphenyl)-1,3-thiazol-5-yl](1,2-oxazolidin-2-yl)methanone,
- [2-(3-fluorophenyl)-4-hydroxy-1,3-thiazol-5-yl](1,3-oxazolidin-3-yl)methanone,
- [4-hydroxy-2-(2-hydroxyphenyl)-1,3-thiazol-5-yl](1,3-oxazolidin-3-yl)methanone,
- [2-(3-fluorophenyl)-4-hydroxy-1,3-thiazol-5-yl](oxolan-2-yl)methanone,
- [4-hydroxy-2-(2-hydroxyphenyl)-1,3-thiazol-5-yl](oxolan-2-yl)methanone,
- [2-(3-fluorophenyl)-4-hydroxy-1,3-thiazol-5-yl](pyrrolidin-1-yl)methanone,
- [4-hydroxy-2-(2-hydroxyphenyl)-1,3-thiazol-5-yl](1,2-oxazinan-2-yl)methanone,
- [2-(3-fluorophenyl)-4-hydroxy-1,3-thiazol-5-yl](1,2-oxazinan-2-yl)methanone,
- [2-(3-fluorophenyl)-4-hydroxy-1,3-thiazol-5-yl](1,3-oxazinan-3-yl)methanone,
- [4-hydroxy-2-(2-hydroxyphenyl)-1,3-thiazol-5-yl](1,3-oxazinan-3-yl)methanone,
- [2-(3-fluorophenyl)-4-hydroxy-1,3-thiazol-5-yl](morpholin-4-yl)methanone,
- [4-hydroxy-2-(2-hydroxyphenyl)-1,3-thiazol-5-yl](morpholin-4-yl)methanone,
- [2-(3-fluorophenyl)-4-hydroxy-1,3-thiazol-5-yl](piperidin-1-yl)methanone,
- [2-(3-fluorophenyl)-4-hydroxy-1,3-thiazol-5-yl](pyrrolidin-2-yl)methanone,
- [2-(3-fluorophenyl)-4-hydroxy-1,3-thiazol-5-yl](1-methylpyrrolidin-2-yl)methanone,
- [2-(3-fluorophenyl)-4-hydroxy-1,3-thiazol-5-yl](1H-pyrrol-2-yl)methanone,
- [2-(3-fluorophenyl)-4-hydroxy-1,3-thiazol-5-yl](1-methyl-1H-pyrrol-2-yl)methanone,
- [2-(3-fluorophenyl)-4-hydroxy-1,3-thiazol-5-yl](furan-2-yl)methanone,
- [2-(3-fluorophenyl)-4-hydroxy-1,3-thiazol-5-yl](thiophen-2-yl)methanone,
- [2-(3-fluorophenyl)-4-hydroxy-1,3-thiazol-5-yl](1H-pyrrol-1-yl)methanone,
- [2-(3-fluorophenyl)-4-hydroxy-1,3-thiazol-5-yl](pyridin-2-yl)methanone,
- [2-(3-fluorophenyl)-4-hydroxy-1,3-thiazol-5-yl](pyridin-3-yl)methanone,
- [2-(3-fluorophenyl)-4-hydroxy-1,3-thiazol-5-yl](pyridin-4-yl)methanone,
- [2-(3-fluorophenyl)-4-hydroxy-1,3-thiazol-5-yl](1H-imidazol-1-yl)methanone,
- [2-(3-fluorophenyl)-4-hydroxy-1,3-thiazol-5-yl](1H-pyrazol-1-yl)methanone,
- [2-(3-fluorophenyl)-4-hydroxy-1,3-thiazol-5-yl](1,2-oxazepan-2-yl)methanone,
- [2-(3-fluorophenyl)-4-hydroxy-1,3-thiazol-5-yl](5-oxa-6-azaspiro[2.4]heptan-6-yl)methanone,
- [2-(3-fluorophenyl)-4-hydroxy-1,3-thiazol-5-yl](5-methyl-1,2-oxazolidin-2-yl)methanone,
- [2-(3-fluorophenyl)-4-hydroxy-1,3-thiazol-5-yl](hexahydro-2H-cyclopenta[d][1,2]oxazol-2-yl)methanone,
- [2-(3-fluorophenyl)-4-hydroxy-1,3-thiazol-5-yl](1H-1,2,3-triazol-1-yl)methanone and
- [2-(3-fluorophenyl)-4-hydroxy-1,3-thiazol-5-yl](1-methyl-1H-tetrazol-5-yl)methanone.

11. The compound according to claim 1, which is selected from the group consisting of:
- [2-(3-fluorophenyl)-4-hydroxy-1,3-thiazol-5-yl](1,2-oxazolidin-2-yl)methanone,
- [4-hydroxy-2-(2-hydroxyphenyl)-1,3-thiazol-5-yl](1,2-oxazolidin-2-yl)methanone,
- [4-hydroxy-2-(2-hydroxyphenyl)-1,3-thiazol-5-yl](1,2-oxazinan-2-yl)methanone and
- [2-(3-fluorphenyl)-4-hydroxy-1,3-thiazol-5-yl](1,2-oxazinan-2-yl)methanone.

12. A method of treating a disease associated with the overexpression and/or hyperactivity of TRPM8, wherein the disease is selected from the group consisting of pain, itch, irritable bowel diseases, cold induced and/or exhacerbated respiratory disorders, ischaemia, stroke, urological disorders, psychiatric disorders and corneal disorders associated with disturbances in the production of the tears and/or altered blinking in a subject in need thereof, comprising administration of an effective amount of the compound according to claim 1.

13. The method according to claim 12, wherein the disease is selected from the group consisting of chronic pain, cancer pain, neuropathic pain, cold allodynia, postoperative pain, neuralgia, neuropathies, diabetic neuropathy, fibromyalgia, algesia, pain associated with nerve injury, migraine, headache, pain associated with osteoarthritis and rheumatoid arthritis, itch, irritable bowel disease, painful bladder syndrome, interstitial cystitis, detrusor overactivity, urinary incontinence, neurogenic detrusor overactivity, idiopathic detrusor overactivity, benign prostatic hyperplasia, lower urinary tract disorders, anxiety, depression and cold-induced/or exhacerbated pulmonary hypertension, COPD, asthma, epiphora and dry eye disease.

14. A pharmaceutical composition comprising as the active ingredient at least one compound according to claim 1 in combination with pharmaceutically acceptable excipients and/or diluents.

* * * * *

UNITED STATES PATENT AND TRADEMARK OFFICE
CERTIFICATE OF CORRECTION

PATENT NO. : 10,246,448 B2
APPLICATION NO. : 16/061850
DATED : April 2, 2019
INVENTOR(S) : Andrea Aramini, Gianluca Bianchini and Samuele Lillini Page 1 of 1

It is certified that error appears in the above-identified patent and that said Letters Patent is hereby corrected as shown below:

On the Title Page

At Column 1, Line 6, Other Publications, the fourth reference: "Wnat" should read -- What --.

Signed and Sealed this
Twenty-eighth Day of May, 2019

Andrei Iancu
*Director of the United States Patent and Trademark Office*